United States Patent
Bourang

(12) United States Patent (10) Patent No.: US 9,254,210 B2
Bourang (45) Date of Patent: Feb. 9, 2016

(54) MULTI-STENT AND MULTI-BALLOON APPARATUS FOR TREATING BIFURCATIONS AND METHODS OF USE

(71) Applicant: Advanced Bifurcation Systems, Inc., Los Angeles, CA (US)

(72) Inventor: Henry Bourang, Turlock, CA (US)

(73) Assignee: Advanced Bifurcation Systems, Inc., Los Angeles, CA (US)

( * ) Notice: Subject to any disclaimer, the term of this patent is extended or adjusted under 35 U.S.C. 154(b) by 302 days.

(21) Appl. No.: 13/796,466

(22) Filed: Mar. 12, 2013

(65) Prior Publication Data

US 2013/0268047 A1 Oct. 10, 2013

Related U.S. Application Data

(63) Continuation of application No. PCT/US2012/024366, filed on Feb. 8, 2012.

(60) Provisional application No. 61/440,742, filed on Feb. 8, 2011.

(51) Int. Cl.
 A61F 2/954 (2013.01)
 A61F 2/95 (2013.01)
 (Continued)

(52) U.S. Cl.
 CPC .................. *A61F 2/954* (2013.01); *A61F 2/958* (2013.01); *A61F 2/852* (2013.01);
 (Continued)

(58) Field of Classification Search
 CPC ........... A61F 2/06; A61F 2/852; A61F 2/954; A61F 2/958; A61F 2/856; A61F 2002/826; A61F 2002/065; A61F 2002/067; A61F 2002/61; A61F 2/95; A61F 2002/061; A61M 2025/0004; A61M 2025/045; A61M 25/104

USPC ....................................... 623/1.35, 1.11, 1.16
See application file for complete search history.

(56) References Cited

U.S. PATENT DOCUMENTS 4,069,825 A 1/1978 Akiyama
4,468,224 A 8/1984 Enzmann et al.
(Continued)

FOREIGN PATENT DOCUMENTS

CN 1441654 A 10/2003
CN 1867374 A 11/2006
(Continued)

OTHER PUBLICATIONS

Office Action of Japanese Patent Application No. 2011-529290, mailed Sep. 25, 2013, 5 pages.
(Continued)

*Primary Examiner* — Katrina Stransky
*Assistant Examiner* — Katherine Schwiker
(74) *Attorney, Agent, or Firm* — Kilpatrick Townsend and Stockton LLP

(57) ABSTRACT

A system for treating a bifurcated vessel that includes a first delivery catheter and a second delivery catheter. The first delivery catheter carries a proximal first stent and a distal second stent. The first delivery catheter also has a first elongate shaft, a proximal first expandable member with the proximal first stent disposed thereover, and a distal second expandable member with the distal second stent disposed thereover. The proximal first expandable member and distal second expandable member are independently expandable of one another. The second delivery catheter carries a third stent. The second delivery catheter also has a second elongate shaft, and a third expandable member with the third stent disposed thereover. The third expandable member is independently expandable of the proximal first expandable member and the distal second expandable member.

19 Claims, 18 Drawing Sheets

(51) Int. Cl.
*A61F 2/06* (2013.01)
*A61F 2/958* (2013.01)
*A61F 2/852* (2013.01)
*A61F 2/82* (2013.01)
*A61M 25/10* (2013.01)
*A61M 25/00* (2006.01)

(52) U.S. Cl.
CPC .... *A61F 2002/061* (2013.01); *A61F 2002/826* (2013.01); *A61M 25/104* (2013.01); *A61M 2025/0004* (2013.01); *A61M 2025/1045* (2013.01)

(56) References Cited

U.S. PATENT DOCUMENTS

| | | |
|---|---|---|
| 4,512,338 A | 4/1985 | Balko |
| 4,564,014 A | 1/1986 | Fogarty et al. |
| 4,580,568 A | 4/1986 | Gianturco |
| 4,681,110 A | 7/1987 | Wiktor |
| 4,690,684 A | 9/1987 | McGreevy et al. |
| 4,733,665 A | 3/1988 | Palmaz |
| 4,739,762 A | 4/1988 | Palmaz |
| 4,762,129 A | 8/1988 | Bonzel |
| 4,770,176 A | 9/1988 | McGreevy et al. |
| 4,775,337 A | 10/1988 | Van Wagener et al. |
| 4,776,337 A | 10/1988 | Palmaz |
| 4,886,062 A | 12/1989 | Wiktor |
| 4,891,225 A | 1/1990 | Langer et al. |
| 4,988,356 A | 1/1991 | Crittenden et al. |
| 4,994,066 A | 2/1991 | Voss |
| 4,994,069 A | 2/1991 | Ritchart et al. |
| 5,013,318 A | 5/1991 | Spranza, III |
| 5,040,548 A | 8/1991 | Yock |
| 5,064,435 A | 11/1991 | Porter |
| 5,092,877 A | 3/1992 | Pinchuk |
| 5,102,417 A | 4/1992 | Palmaz |
| 5,104,404 A | 4/1992 | Wolff |
| 5,122,154 A | 6/1992 | Rhodes |
| 5,135,535 A | 8/1992 | Kramer |
| 5,195,984 A | 3/1993 | Schatz |
| 5,217,495 A | 6/1993 | Kaplan et al. |
| 5,219,355 A | 6/1993 | Parodi et al. |
| 5,226,913 A | 7/1993 | Pinchuk |
| 5,246,421 A | 9/1993 | Saab |
| 5,273,536 A | 12/1993 | Savas |
| 5,282,824 A | 2/1994 | Gianturco |
| 5,300,085 A | 4/1994 | Yock |
| 5,312,415 A | 5/1994 | Palermo |
| 5,334,187 A | 8/1994 | Fischell et al. |
| 5,403,341 A | 4/1995 | Solar |
| 5,421,955 A | 6/1995 | Lau et al. |
| 5,456,694 A | 10/1995 | Marin et al. |
| 5,456,713 A | 10/1995 | Chuter |
| 5,458,615 A | 10/1995 | Klemm et al. |
| 5,478,349 A | 12/1995 | Nicholas |
| 5,490,837 A | 2/1996 | Blaeser et al. |
| 5,496,346 A | 3/1996 | Horzewski et al. |
| 5,501,227 A | 3/1996 | Yock |
| 5,507,768 A | 4/1996 | Lau et al. |
| 5,507,771 A | 4/1996 | Gianturco |
| 5,514,093 A | 5/1996 | Ellis et al. |
| 5,514,154 A | 5/1996 | Lau et al. |
| 5,527,354 A | 6/1996 | Fontaine et al. |
| 5,549,551 A | 8/1996 | Peacock, III et al. |
| 5,549,563 A | 8/1996 | Kronner |
| 5,549,635 A | 8/1996 | Solar |
| 5,554,181 A | 9/1996 | Das |
| 5,562,725 A | 10/1996 | Schmitt et al. |
| 5,571,086 A | 11/1996 | Kaplan et al. |
| 5,593,412 A | 1/1997 | Martinez et al. |
| 5,607,444 A | 3/1997 | Lam |
| 5,607,463 A | 3/1997 | Schwartz et al. |
| 5,609,627 A | 3/1997 | Goicoechea et al. |
| 5,628,775 A | 5/1997 | Jackson et al. |
| 5,632,763 A | 5/1997 | Glastra |
| 5,632,772 A | 5/1997 | Alcime et al. |
| 5,634,928 A | 6/1997 | Fischell et al. |
| 5,639,274 A | 6/1997 | Fischell et al. |
| 5,662,675 A | 9/1997 | Polanskyj Stockert et al. |
| 5,669,924 A | 9/1997 | Shaknovich |
| 5,670,161 A | 9/1997 | Healy et al. |
| 5,676,654 A | 10/1997 | Ellis et al. |
| 5,683,451 A | 11/1997 | Lenker et al. |
| 5,697,948 A | 12/1997 | Marin et al. |
| 5,697,967 A | 12/1997 | Dinh et al. |
| 5,702,418 A | 12/1997 | Ravenscroft |
| 5,709,701 A | 1/1998 | Parodi |
| 5,716,393 A | 2/1998 | Lindenberg et al. |
| 5,722,669 A | 3/1998 | Shimizu et al. |
| 5,723,003 A | 3/1998 | Winston et al. |
| 5,735,869 A | 4/1998 | Fernandez-Aceytuno |
| 5,741,323 A | 4/1998 | Pathak et al. |
| 5,749,848 A | 5/1998 | Jang et al. |
| 5,749,921 A | 5/1998 | Lenker et al. |
| 5,755,735 A | 5/1998 | Richter et al. |
| 5,755,771 A | 5/1998 | Penn et al. |
| 5,755,772 A | 5/1998 | Evans et al. |
| 5,755,776 A | 5/1998 | Al-Saadon |
| 5,755,781 A | 5/1998 | Jayaraman |
| 5,769,882 A | 6/1998 | Fogarty et al. |
| 5,772,669 A | 6/1998 | Vrba |
| 5,776,141 A | 7/1998 | Klein et al. |
| 5,797,951 A | 8/1998 | Mueller et al. |
| 5,800,519 A | 9/1998 | Sandock |
| 5,807,398 A | 9/1998 | Shaknovich |
| 5,824,040 A | 10/1998 | Cox et al. |
| 5,824,041 A | 10/1998 | Lenker et al. |
| 5,827,320 A | 10/1998 | Richter et al. |
| 5,833,694 A | 11/1998 | Poncet |
| 5,836,964 A | 11/1998 | Richter et al. |
| 5,843,092 A | 12/1998 | Heller et al. |
| 5,855,563 A | 1/1999 | Kaplan et al. |
| 5,858,556 A | 1/1999 | Eckert et al. |
| 5,870,381 A | 2/1999 | Kawasaki et al. |
| 5,879,370 A | 3/1999 | Fischell et al. |
| 5,891,190 A | 4/1999 | Boneau |
| 5,893,887 A | 4/1999 | Jayaraman |
| 5,895,398 A | 4/1999 | Wensel et al. |
| 5,899,935 A | 5/1999 | Ding |
| 5,902,332 A | 5/1999 | Schatz |
| 5,911,754 A | 6/1999 | Kanesaka et al. |
| 5,919,175 A | 7/1999 | Sirhan |
| 5,922,020 A | 7/1999 | Klein et al. |
| 5,961,536 A | 10/1999 | Mickley et al. |
| 5,968,069 A | 10/1999 | Dusbabek et al. |
| 5,972,027 A | 10/1999 | Johnson |
| 5,976,107 A | 11/1999 | Mertens et al. |
| 5,976,155 A | 11/1999 | Foreman et al. |
| 5,980,484 A | 11/1999 | Ressemann et al. |
| 5,980,486 A | 11/1999 | Enger |
| 5,980,514 A | 11/1999 | Kupiecki et al. |
| 5,980,552 A | 11/1999 | Pinchasik et al. |
| 5,984,957 A | 11/1999 | Laptewicz, Jr. et al. |
| 5,997,563 A | 12/1999 | Kretzers et al. |
| 6,004,328 A | 12/1999 | Solar |
| 6,007,517 A | 12/1999 | Anderson |
| 6,017,363 A | 1/2000 | Hojeibane |
| 6,022,359 A | 2/2000 | Frantzen |
| 6,022,374 A | 2/2000 | Imran |
| 6,033,434 A | 3/2000 | Borghi |
| 6,036,725 A | 3/2000 | Avellanet |
| 6,039,721 A | 3/2000 | Johnson et al. |
| 6,042,589 A | 3/2000 | Marianne |
| 6,048,361 A | 4/2000 | Oepen |
| 6,056,722 A | 5/2000 | Jayaraman |
| 6,056,775 A | 5/2000 | Borghi et al. |
| 6,059,811 A | 5/2000 | Pinchasik et al. |
| 6,059,824 A | 5/2000 | Taheri |
| 6,066,155 A | 5/2000 | Amann et al. |
| 6,068,655 A | 5/2000 | Seguin et al. |
| 6,070,589 A | 6/2000 | Keith et al. |
| 6,086,604 A | 7/2000 | Fischell et al. |
| 6,090,063 A | 7/2000 | Makower et al. |

(56) References Cited

U.S. PATENT DOCUMENTS

| | | |
|---|---|---|
| 6,090,136 A | 7/2000 | McDonald et al. |
| 6,096,071 A | 8/2000 | Yadav |
| 6,096,073 A | 8/2000 | Webster et al. |
| 6,099,497 A | 8/2000 | Adams et al. |
| 6,102,942 A | 8/2000 | Ahari |
| 6,106,530 A | 8/2000 | Harada |
| RE36,857 E | 9/2000 | Euteneuer et al. |
| 6,117,117 A | 9/2000 | Mauch |
| 6,120,522 A | 9/2000 | Vrba et al. |
| 6,123,712 A | 9/2000 | Di Caprio et al. |
| 6,123,723 A | 9/2000 | Konya et al. |
| 6,126,685 A | 10/2000 | Lenker et al. |
| 6,129,738 A | 10/2000 | Lashinski et al. |
| 6,129,756 A | 10/2000 | Kugler |
| 6,132,460 A | 10/2000 | Thompson |
| 6,142,973 A | 11/2000 | Carleton et al. |
| 6,143,016 A | 11/2000 | Bleam et al. |
| 6,165,167 A | 12/2000 | Delaloye |
| 6,165,210 A | 12/2000 | Lau et al. |
| 6,179,878 B1 | 1/2001 | Duering |
| 6,183,509 B1 | 2/2001 | Dibie |
| 6,187,034 B1 | 2/2001 | Frantzen |
| 6,190,402 B1 | 2/2001 | Horton et al. |
| 6,196,995 B1 | 3/2001 | Fagan |
| 6,200,337 B1 | 3/2001 | Moriuchi et al. |
| 6,210,429 B1 | 4/2001 | Vardi et al. |
| 6,238,991 B1 | 5/2001 | Suzuki |
| 6,241,691 B1 | 6/2001 | Ferrera et al. |
| 6,251,132 B1 | 6/2001 | Ravenscroft et al. |
| 6,251,134 B1 | 6/2001 | Alt et al. |
| 6,254,612 B1 | 7/2001 | Hieshima |
| 6,254,628 B1 | 7/2001 | Wallace et al. |
| 6,258,117 B1 | 7/2001 | Camrud et al. |
| 6,264,682 B1 | 7/2001 | Wilson et al. |
| 6,264,688 B1 | 7/2001 | Herklotz et al. |
| 6,267,783 B1 | 7/2001 | Letendre et al. |
| 6,273,895 B1 | 8/2001 | Pinchuk et al. |
| 6,273,911 B1 | 8/2001 | Cox et al. |
| 6,273,913 B1 | 8/2001 | Wright et al. |
| 6,312,458 B1 | 11/2001 | Golds |
| 6,315,794 B1 | 11/2001 | Richter |
| 6,319,277 B1 | 11/2001 | Rudnick et al. |
| 6,322,586 B1 | 11/2001 | Monroe et al. |
| 6,325,823 B1 | 12/2001 | Horzewski et al. |
| 6,325,826 B1 | 12/2001 | Vardi et al. |
| 6,334,871 B1 | 1/2002 | Dor et al. |
| 6,344,053 B1 | 2/2002 | Boneau |
| 6,344,056 B1 | 2/2002 | Dehdashtian |
| 6,344,272 B1 | 2/2002 | Oldenburg et al. |
| 6,357,104 B1 | 3/2002 | Myers |
| 6,361,555 B1 | 3/2002 | Wilson |
| 6,375,676 B1 | 4/2002 | Cox |
| 6,379,365 B1 | 4/2002 | Diaz |
| 6,383,171 B1 | 5/2002 | Gifford et al. |
| 6,398,807 B1 | 6/2002 | Chouinard et al. |
| 6,409,753 B1 | 6/2002 | Brown et al. |
| 6,415,696 B1 | 7/2002 | Erickeson et al. |
| 6,419,693 B1 | 7/2002 | Fariabi |
| 6,428,811 B1 | 8/2002 | West et al. |
| 6,443,982 B1 | 9/2002 | Israel et al. |
| 6,451,025 B1 | 9/2002 | Jervis |
| 6,451,050 B1 | 9/2002 | Rudakov et al. |
| 6,464,720 B2 | 10/2002 | Boatman et al. |
| 6,468,298 B1 | 10/2002 | Pelton |
| 6,468,299 B2 | 10/2002 | Stack et al. |
| 6,485,510 B1 | 11/2002 | Camrud et al. |
| 6,485,511 B2 | 11/2002 | Lau et al. |
| 6,488,694 B1 | 12/2002 | Lau et al. |
| 6,488,702 B1 | 12/2002 | Besselink |
| 6,488,703 B1 | 12/2002 | Kveen et al. |
| 6,511,468 B1 | 1/2003 | Cragg et al. |
| 6,514,281 B1 | 2/2003 | Blaeser et al. |
| 6,520,986 B2 | 2/2003 | Martin et al. |
| 6,520,987 B1 | 2/2003 | Plante |
| 6,520,988 B1 | 2/2003 | Colombo et al. |
| 6,527,789 B1 | 3/2003 | Lau et al. |
| 6,527,799 B2 | 3/2003 | Shanley |
| 6,530,944 B2 | 3/2003 | West et al. |
| 6,540,777 B2 | 4/2003 | Stenzel |
| 6,540,779 B2 | 4/2003 | Richter et al. |
| 6,551,350 B1 | 4/2003 | Thornton et al. |
| 6,555,157 B1 | 4/2003 | Hossainy |
| 6,569,180 B1 | 5/2003 | Sirhan et al. |
| 6,575,993 B1 | 6/2003 | Yock |
| 6,579,305 B1 | 6/2003 | Lashinski |
| 6,579,309 B1 | 6/2003 | Loos et al. |
| 6,582,394 B1 | 6/2003 | Reiss et al. |
| 6,582,460 B1 | 6/2003 | Cryer |
| 6,585,756 B1 | 7/2003 | Strecker |
| 6,592,549 B2 | 7/2003 | Gerdts et al. |
| 6,596,020 B2 | 7/2003 | Vardi et al. |
| 6,596,022 B2 | 7/2003 | Lau et al. |
| 6,599,296 B1 | 7/2003 | Gillick et al. |
| 6,599,314 B2 | 7/2003 | Mathis |
| 6,602,282 B1 | 8/2003 | Yan |
| 6,605,062 B1 | 8/2003 | Hurley et al. |
| 6,605,109 B2 | 8/2003 | Fiedler |
| 6,607,553 B1 | 8/2003 | Healy et al. |
| 6,645,517 B2 | 11/2003 | West |
| 6,645,547 B1 | 11/2003 | Shekalim et al. |
| 6,656,212 B2 | 12/2003 | Ravenscroft et al. |
| 6,660,031 B2 | 12/2003 | Tran et al. |
| 6,660,381 B2 | 12/2003 | Halas et al. |
| 6,666,883 B1 | 12/2003 | Seguin et al. |
| 6,676,695 B2 | 1/2004 | Solem |
| 6,679,909 B2 | 1/2004 | McIntosh et al. |
| 6,685,721 B1 | 2/2004 | Kramer |
| 6,685,730 B2 | 2/2004 | West et al. |
| 6,689,156 B1 | 2/2004 | Davidson et al. |
| 6,692,465 B2 | 2/2004 | Kramer |
| 6,692,483 B2 | 2/2004 | Vardi et al. |
| 6,699,280 B2 | 3/2004 | Camrud et al. |
| 6,699,724 B1 | 3/2004 | West et al. |
| 6,702,843 B1 | 3/2004 | Brown |
| 6,706,062 B2 | 3/2004 | Vardi et al. |
| 6,709,379 B1 | 3/2004 | Brandau et al. |
| 6,709,440 B2 | 3/2004 | Callol et al. |
| 6,712,827 B2 | 3/2004 | Ellis et al. |
| 6,712,845 B2 | 3/2004 | Hossainy |
| 6,723,071 B2 | 4/2004 | Gerdts et al. |
| 6,736,842 B2 | 5/2004 | Healy et al. |
| 6,749,628 B1 | 6/2004 | Callol et al. |
| 6,761,734 B2 | 7/2004 | Suhr |
| 6,770,091 B2 | 8/2004 | Richter et al. |
| 6,778,316 B2 | 8/2004 | Halas et al. |
| 6,800,065 B2 | 10/2004 | Duane et al. |
| 6,811,566 B1 | 11/2004 | Penn et al. |
| 6,825,203 B2 | 11/2004 | Pasternak et al. |
| 6,835,203 B1 | 12/2004 | Vardi et al. |
| 6,837,901 B2 | 1/2005 | Rabkin et al. |
| 6,849,084 B2 | 2/2005 | Rabkin et al. |
| 6,852,252 B2 | 2/2005 | Halas et al. |
| 6,855,125 B2 | 2/2005 | Shanley |
| 6,858,034 B1 | 2/2005 | Hijlkema et al. |
| 6,875,228 B2 | 4/2005 | Pinchasik et al. |
| 6,878,161 B2 | 4/2005 | Lenker |
| 6,879,370 B2 | 4/2005 | Yokoue et al. |
| 6,884,258 B2 | 4/2005 | Vardi et al. |
| 6,893,417 B2 | 5/2005 | Gribbons et al. |
| 6,896,695 B2 | 5/2005 | Mueller et al. |
| 6,908,477 B2 | 6/2005 | McGuckin, Jr. et al. |
| 6,918,928 B2 | 7/2005 | Wolinsky et al. |
| 6,939,376 B2 | 9/2005 | Shulz et al. |
| 6,945,989 B1 | 9/2005 | Betelia et al. |
| 6,945,995 B2 | 9/2005 | Nicholas |
| 6,949,120 B2 | 9/2005 | Kveen et al. |
| 6,951,053 B2 | 10/2005 | Padilla et al. |
| 6,955,687 B2 | 10/2005 | Richter et al. |
| 6,955,688 B2 | 10/2005 | Wilson et al. |
| 6,962,602 B2 | 11/2005 | Vardi et al. |
| 6,989,026 B2 | 1/2006 | Richter et al. |
| 7,005,454 B2 | 2/2006 | Brocchini et al. |
| 7,037,327 B2 | 5/2006 | Salmon et al. |
| 7,090,694 B1 | 8/2006 | Morris et al. |

(56) References Cited

U.S. PATENT DOCUMENTS

| | | |
|---|---|---|
| 7,101,840 B2 | 9/2006 | Brocchini et al. |
| 7,137,993 B2 | 11/2006 | Acosta et al. |
| 7,147,655 B2 | 12/2006 | Chermoni |
| 7,147,656 B2 | 12/2006 | Andreas et al. |
| 7,182,779 B2 | 2/2007 | Acosta et al. |
| 7,192,440 B2 | 3/2007 | Andreas et al. |
| 7,220,275 B2 | 5/2007 | Davidson et al. |
| 7,241,308 B2 | 7/2007 | Andreas et al. |
| 7,270,668 B2 | 9/2007 | Andreas et al. |
| 7,294,146 B2 | 11/2007 | Chew et al. |
| 7,300,456 B2 | 11/2007 | Andreas et al. |
| 7,309,350 B2 | 12/2007 | Landreville et al. |
| 7,314,480 B2 | 1/2008 | Eidenschink et al. |
| 7,320,702 B2 | 1/2008 | Hammersmark et al. |
| 7,323,006 B2 | 1/2008 | Andreas et al. |
| 7,323,009 B2 | 1/2008 | Suhr et al. |
| 7,326,236 B2 | 2/2008 | Andreas et al. |
| 7,326,242 B2 | 2/2008 | Eidenschink |
| 7,341,598 B2 | 3/2008 | Davidson et al. |
| 7,344,556 B2 * | 3/2008 | Seguin .................. A61F 2/915 623/1.11 |
| 7,387,639 B2 | 6/2008 | Bourang et al. |
| 7,445,688 B2 | 11/2008 | Suzuki et al. |
| 7,520,895 B2 | 4/2009 | Douglas et al. |
| 7,537,609 B2 | 5/2009 | Davidson et al. |
| 7,540,881 B2 | 6/2009 | Meyer et al. |
| 7,635,383 B2 | 12/2009 | Gumm |
| 7,641,684 B2 | 1/2010 | Hilaire et al. |
| 7,641,685 B2 | 1/2010 | Richter |
| 7,695,508 B2 | 4/2010 | Der Leest et al. |
| 8,016,870 B2 | 9/2011 | Chew et al. |
| 8,070,789 B2 | 12/2011 | Will et al. |
| 8,769,796 B2 | 7/2014 | Bourang et al. |
| 8,795,347 B2 | 8/2014 | Bourang et al. |
| 8,808,347 B2 | 8/2014 | Bourang et al. |
| 8,821,562 B2 | 9/2014 | Bourang et al. |
| 8,828,071 B2 | 9/2014 | Bourang et al. |
| 8,979,917 B2 | 3/2015 | Bourang et al. |
| 2001/0003161 A1 | 6/2001 | Vardi et al. |
| 2001/0020154 A1 | 9/2001 | Bigus et al. |
| 2001/0020181 A1 | 9/2001 | Layne |
| 2001/0044595 A1 | 11/2001 | Reydel et al. |
| 2001/0044622 A1 | 11/2001 | Vardi et al. |
| 2001/0044632 A1 | 11/2001 | Daniel et al. |
| 2001/0049547 A1 | 12/2001 | Moore |
| 2002/0037358 A1 | 3/2002 | Barry et al. |
| 2002/0091439 A1 | 7/2002 | Baker et al. |
| 2002/0107560 A1 | 8/2002 | Richter |
| 2002/0111671 A1 | 8/2002 | Stenzel |
| 2002/0128706 A1 | 9/2002 | Osypka |
| 2002/0138132 A1 | 9/2002 | Brown |
| 2002/0143382 A1 | 10/2002 | Hijlkema et al. |
| 2002/0151924 A1 | 10/2002 | Shiber |
| 2002/0151955 A1 | 10/2002 | Tran et al. |
| 2002/0156496 A1 | 10/2002 | Chermoni |
| 2002/0173835 A1 | 11/2002 | Bourang et al. |
| 2002/0177890 A1 | 11/2002 | Lenker |
| 2002/0183763 A1 | 12/2002 | Callol et al. |
| 2002/0188343 A1 | 12/2002 | Mathis |
| 2002/0188347 A1 | 12/2002 | Mathis |
| 2002/0193873 A1 | 12/2002 | Brucker et al. |
| 2003/0028233 A1 | 2/2003 | Vardi et al. |
| 2003/0029039 A1 | 2/2003 | Richter et al. |
| 2003/0045923 A1 | 3/2003 | Bashiri et al. |
| 2003/0093143 A1 | 5/2003 | Zhao et al. |
| 2003/0097169 A1 | 5/2003 | Brucker et al. |
| 2003/0114912 A1 | 6/2003 | Sequin et al. |
| 2003/0114919 A1 | 6/2003 | McQuiston et al. |
| 2003/0114922 A1 | 6/2003 | Iwasaka et al. |
| 2003/0125791 A1 | 7/2003 | Sequin et al. |
| 2003/0125800 A1 | 7/2003 | Shulze et al. |
| 2003/0125802 A1 | 7/2003 | Callol et al. |
| 2003/0135259 A1 | 7/2003 | Simso |
| 2003/0135266 A1 | 7/2003 | Chew et al. |
| 2003/0139796 A1 | 7/2003 | Sequin et al. |
| 2003/0139797 A1 | 7/2003 | Johnson et al. |
| 2003/0139798 A1 | 7/2003 | Brown et al. |
| 2003/0163085 A1 | 8/2003 | Tanner et al. |
| 2003/0176909 A1 | 9/2003 | Kusleika |
| 2003/0191516 A1 | 10/2003 | Weldon et al. |
| 2003/0192164 A1 | 10/2003 | Austin |
| 2003/0195609 A1 | 10/2003 | Berenstein |
| 2003/0199821 A1 | 10/2003 | Gerdts et al. |
| 2003/0204238 A1 | 10/2003 | Tedeschi |
| 2003/0212447 A1 | 11/2003 | Euteneuer |
| 2003/0225446 A1 | 12/2003 | Hartley |
| 2004/0024450 A1 | 2/2004 | Shulze et al. |
| 2004/0030380 A1 | 2/2004 | Shulze et al. |
| 2004/0044395 A1 | 3/2004 | Nelson |
| 2004/0044398 A1 | 3/2004 | Nicholas |
| 2004/0087965 A1 | 5/2004 | Levine et al. |
| 2004/0093061 A1 | 5/2004 | Acosta et al. |
| 2004/0093067 A1 | 5/2004 | Israel |
| 2004/0093077 A1 | 5/2004 | White et al. |
| 2004/0098081 A1 | 5/2004 | Landreville et al. |
| 2004/0106979 A1 | 6/2004 | Goicoechea |
| 2004/0111145 A1 | 6/2004 | Serino et al. |
| 2004/0117008 A1 | 6/2004 | Wnendt et al. |
| 2004/0176832 A1 | 9/2004 | Hartley et al. |
| 2004/0186551 A1 | 9/2004 | Kao et al. |
| 2004/0193245 A1 | 9/2004 | Deem et al. |
| 2004/0215165 A1 | 10/2004 | Coyle et al. |
| 2004/0215312 A1 | 10/2004 | Andreas et al. |
| 2004/0243217 A1 | 12/2004 | Andersen et al. |
| 2004/0249434 A1 | 12/2004 | Andreas et al. |
| 2004/0249435 A1 | 12/2004 | Andreas et al. |
| 2005/0010276 A1 | 1/2005 | Acosta et al. |
| 2005/0038505 A1 | 2/2005 | Shuize et al. |
| 2005/0049673 A1 | 3/2005 | Andreas et al. |
| 2005/0049680 A1 | 3/2005 | Fischell et al. |
| 2005/0080474 A1 | 4/2005 | Andreas et al. |
| 2005/0080475 A1 | 4/2005 | Andreas et al. |
| 2005/0085845 A1 | 4/2005 | Hilaire et al. |
| 2005/0090846 A1 | 4/2005 | Pedersen et al. |
| 2005/0101624 A1 | 5/2005 | Betts et al. |
| 2005/0125051 A1 | 6/2005 | Eidenschink et al. |
| 2005/0131008 A1 | 6/2005 | Betts et al. |
| 2005/0133164 A1 | 6/2005 | Fischer et al. |
| 2005/0143827 A1 | 6/2005 | Globerman et al. |
| 2005/0149159 A1 | 7/2005 | Andreas et al. |
| 2005/0165378 A1 | 7/2005 | Heinrich et al. |
| 2005/0182473 A1 | 8/2005 | Eidenschink et al. |
| 2005/0183259 A1 | 8/2005 | Eidenschink et al. |
| 2005/0197688 A1 | 9/2005 | Theron et al. |
| 2005/0209674 A1 | 9/2005 | Kutscher et al. |
| 2005/0222671 A1 | 10/2005 | Schaeffer et al. |
| 2005/0228477 A1 | 10/2005 | Grainger et al. |
| 2005/0245637 A1 | 11/2005 | Hossainy et al. |
| 2005/0288763 A1 | 12/2005 | Andreas et al. |
| 2005/0288764 A1 | 12/2005 | Snow et al. |
| 2005/0288766 A1 | 12/2005 | Plain et al. |
| 2006/0069424 A1 | 3/2006 | Acosta et al. |
| 2006/0100694 A1 | 5/2006 | Globerman |
| 2006/0123874 A1 | 6/2006 | Motsenbocker |
| 2006/0200223 A1 | 9/2006 | Andreas et al. |
| 2006/0206190 A1 | 9/2006 | Chermoni |
| 2006/0229700 A1 | 10/2006 | Acosta et al. |
| 2006/0229706 A1 | 10/2006 | Shulze et al. |
| 2006/0271090 A1 * | 11/2006 | Shaked et al. ................ 606/192 |
| 2006/0271150 A1 | 11/2006 | Andreas et al. |
| 2006/0271151 A1 | 11/2006 | McGarry et al. |
| 2006/0282147 A1 | 12/2006 | Andreas et al. |
| 2006/0282149 A1 | 12/2006 | Kao |
| 2006/0282150 A1 | 12/2006 | Olson et al. |
| 2006/0287726 A1 | 12/2006 | Segal et al. |
| 2007/0027521 A1 | 2/2007 | Andreas et al. |
| 2007/0027524 A1 | 2/2007 | Johnson et al. |
| 2007/0055351 A1 | 3/2007 | Eidenschink et al. |
| 2007/0061003 A1 | 3/2007 | Shmulewitz et al. |
| 2007/0067012 A1 | 3/2007 | George et al. |
| 2007/0088368 A1 | 4/2007 | Acosta et al. |
| 2007/0088420 A1 | 4/2007 | Andreas et al. |
| 2007/0088422 A1 | 4/2007 | Chew et al. |
| 2007/0100423 A1 | 5/2007 | Acosta et al. |

(56) References Cited

U.S. PATENT DOCUMENTS

| | | |
|---|---|---|
| 2007/0100424 A1 | 5/2007 | Chew et al. |
| 2007/0106365 A1 | 5/2007 | Andreas et al. |
| 2007/0118202 A1 | 5/2007 | Chermoni |
| 2007/0118203 A1 | 5/2007 | Chermoni |
| 2007/0118204 A1 | 5/2007 | Chermoni |
| 2007/0129733 A1 | 6/2007 | Will et al. |
| 2007/0156225 A1 | 7/2007 | George et al. |
| 2007/0156226 A1 | 7/2007 | Chew et al. |
| 2007/0179587 A1 | 8/2007 | Acosta et al. |
| 2007/0203571 A1 | 8/2007 | Kaplan et al. |
| 2007/0219611 A1 | 9/2007 | Krever et al. |
| 2007/0219612 A1 | 9/2007 | Andreas et al. |
| 2007/0219613 A1 | 9/2007 | Kao et al. |
| 2007/0219625 A1 | 9/2007 | Venturelli et al. |
| 2007/0265637 A1 | 11/2007 | Andreas et al. |
| 2007/0270936 A1 | 11/2007 | Andreas et al. |
| 2007/0276460 A1 | 11/2007 | Davis et al. |
| 2007/0276461 A1 | 11/2007 | Andreas et al. |
| 2007/0281117 A1 | 12/2007 | Kaplan et al. |
| 2007/0282419 A1 | 12/2007 | Hilaire et al. |
| 2007/0292518 A1 | 12/2007 | Ludwig |
| 2008/0009932 A1 | 1/2008 | Ta et al. |
| 2008/0009933 A1 | 1/2008 | Ta et al. |
| 2008/0051869 A1 | 2/2008 | Yribarren |
| 2008/0071345 A1 | 3/2008 | Hammersmark et al. |
| 2008/0077229 A1 | 3/2008 | Andreas et al. |
| 2008/0091257 A1 | 4/2008 | Andreas et al. |
| 2008/0097299 A1 | 4/2008 | Andreas et al. |
| 2008/0097574 A1 | 4/2008 | Andreas et al. |
| 2008/0132989 A1 | 6/2008 | Snow et al. |
| 2008/0147162 A1 | 6/2008 | Andreas et al. |
| 2008/0199510 A1 | 8/2008 | Ruane et al. |
| 2008/0208309 A1 | 8/2008 | Saeed |
| 2008/0208311 A1 | 8/2008 | Kao et al. |
| 2008/0208318 A1 | 8/2008 | Kao et al. |
| 2008/0221655 A1 | 9/2008 | Miller |
| 2008/0234795 A1 | 9/2008 | Snow et al. |
| 2008/0234798 A1 | 9/2008 | Chew et al. |
| 2008/0234799 A1 | 9/2008 | Acosta et al. |
| 2008/0269865 A1 | 10/2008 | Snow et al. |
| 2009/0076584 A1 | 3/2009 | Mao et al. |
| 2009/0105686 A1 | 4/2009 | Snow et al. |
| 2009/0132019 A1 | 5/2009 | Duffy et al. |
| 2009/0143854 A1 | 6/2009 | Adams et al. |
| 2009/0171430 A1 | 7/2009 | Baim et al. |
| 2009/0182270 A1 | 7/2009 | Nanavati |
| 2009/0228088 A1 | 9/2009 | Lowe et al. |
| 2009/0240321 A1 | 9/2009 | Davidson et al. |
| 2009/0254167 A1 | 10/2009 | Ricci et al. |
| 2009/0259285 A1 | 10/2009 | Duane et al. |
| 2009/0287289 A1 | 11/2009 | Sagedahl et al. |
| 2009/0299454 A1 | 12/2009 | Jennings et al. |
| 2009/0319030 A1 | 12/2009 | Yadin et al. |
| 2009/0326641 A1 | 12/2009 | Davis et al. |
| 2010/0004737 A1 | 1/2010 | Eidenschink |
| 2010/0030183 A1 | 2/2010 | Toner et al. |
| 2010/0036477 A1 | 2/2010 | Bronson et al. |
| 2010/0042199 A1 | 2/2010 | Burton |
| 2010/0049298 A1 | 2/2010 | Hamer et al. |
| 2010/0057020 A1 | 3/2010 | Uretsky |
| 2010/0063571 A1 | 3/2010 | Roach et al. |
| 2010/0106238 A1 | 4/2010 | Hilaire et al. |
| 2011/0029061 A1 | 2/2011 | Ahn et al. |
| 2011/0282427 A1 | 11/2011 | Bourang et al. |
| 2011/0307044 A1 | 12/2011 | Bourang et al. |
| 2011/0307045 A1 | 12/2011 | Bourang et al. |
| 2011/0307046 A1 | 12/2011 | Bourang et al. |
| 2011/0307047 A1 | 12/2011 | Bourang et al. |
| 2011/0307052 A1 | 12/2011 | Bourang et al. |
| 2014/0100647 A1 | 4/2014 | Bourang |
| 2015/0032196 A1 | 1/2015 | Bourang et al. |

FOREIGN PATENT DOCUMENTS

| | | |
|---|---|---|
| CN | 101035488 A | 12/2007 |
| CN | 102215780 A | 10/2011 |
| CN | 103037813 A | 4/2013 |
| CN | 103037815 A | 4/2013 |
| CN | 103037816 A | 4/2013 |
| CN | 103037817 A | 4/2013 |
| CN | 103068345 A | 4/2013 |
| EP | 0 203 945 B2 | 12/1986 |
| EP | 0 274 129 B1 | 7/1988 |
| EP | 0 282 143 A1 | 9/1988 |
| EP | 0 505 686 A1 | 9/1992 |
| EP | 0 533 960 A1 | 3/1993 |
| EP | 0 714 640 A1 | 6/1996 |
| EP | 0 596 145 A1 | 5/1997 |
| EP | 0 897 700 A1 | 2/1999 |
| EP | 0 947 180 A2 | 10/1999 |
| EP | 1 258 230 A2 | 11/2002 |
| EP | 1 277 449 A1 | 1/2003 |
| EP | 1 523 959 A2 | 4/2005 |
| EP | 1 523 960 A2 | 4/2005 |
| EP | 1 266 638 A2 | 10/2005 |
| EP | 1788977 B1 | 3/2008 |
| EP | 1 905 398 A2 | 4/2008 |
| EP | 2344068 A1 | 7/2011 |
| EP | 2549949 A1 | 1/2013 |
| EP | 2549950 A1 | 1/2013 |
| EP | 2549951 A1 | 1/2013 |
| EP | 2549952 A1 | 1/2013 |
| EP | 2549958 A1 | 1/2013 |
| EP | 2 672 925 | 12/2013 |
| EP | 2 672 932 | 12/2013 |
| JP | 10-043313 | 2/1998 |
| JP | 2003-532437 A | 11/2003 |
| JP | 2004-528877 A | 9/2004 |
| JP | 2007-508082 A | 4/2007 |
| JP | 2010-503465 A | 4/2010 |
| JP | 2012503534 A | 2/2012 |
| JP | 2013523215 A | 6/2013 |
| WO | 96/26689 A1 | 9/1996 |
| WO | 96/33677 A2 | 10/1996 |
| WO | 97/46174 A1 | 12/1997 |
| WO | 97/48351 A1 | 12/1997 |
| WO | 98/20810 A1 | 5/1998 |
| WO | 98/37833 A1 | 9/1998 |
| WO | 98/58600 A1 | 12/1998 |
| WO | 99/01087 A1 | 1/1999 |
| WO | 00/12832 A2 | 3/2000 |
| WO | 00/15151 A1 | 3/2000 |
| WO | 00/25841 A1 | 5/2000 |
| WO | 00/32136 A1 | 6/2000 |
| WO | 00/41649 A1 | 7/2000 |
| WO | 00/50116 A1 | 8/2000 |
| WO | 00/62708 A1 | 10/2000 |
| WO | 00/72780 A1 | 12/2000 |
| WO | 00/74595 A1 | 12/2000 |
| WO | 01/70297 A2 | 9/2001 |
| WO | 01/91918 A1 | 12/2001 |
| WO | 02/060344 A2 | 8/2002 |
| WO | 02/085253 A1 | 10/2002 |
| WO | 03/022178 A1 | 3/2003 |
| WO | 03/047651 A2 | 6/2003 |
| WO | 03/051425 A2 | 6/2003 |
| WO | 03/055414 | 7/2003 |
| WO | 03/105922 A2 | 12/2003 |
| WO | 2004/017865 A1 | 3/2004 |
| WO | 2004/043299 A1 | 5/2004 |
| WO | 2004/043301 A1 | 5/2004 |
| WO | 2004/043410 A1 | 5/2004 |
| WO | 2004/052237 A2 | 6/2004 |
| WO | 2005/013853 A2 | 2/2005 |
| WO | WO 2005/039681 A1 | 5/2005 |
| WO | 2006/036939 A2 | 4/2006 |
| WO | 2006/047520 A2 | 5/2006 |
| WO | 2007/035805 A2 | 3/2007 |
| WO | 2007/053187 A2 | 5/2007 |
| WO | 2007/146411 A2 | 12/2007 |
| WO | 2008/005111 A1 | 1/2008 |

(56) References Cited

FOREIGN PATENT DOCUMENTS

| | | | |
|---|---|---|---|
| WO | WO 2008/033621 A1 | 3/2008 | |
| WO | WO 2008/130503 A2 | 10/2008 | |
| WO | WO 2009/148594 A1 | 12/2009 | |
| WO | 2010/036982 A1 | 4/2010 | |
| WO | WO 2010/036982 A1 | 4/2010 | |
| WO | 2011/119879 A1 | 9/2011 | |
| WO | 2011/119880 A1 | 9/2011 | |
| WO | 2011/119882 A1 | 9/2011 | |
| WO | 2011/119883 A1 | 9/2011 | |
| WO | 2011/119884 A1 | 9/2011 | |
| WO | 2012/109365 A1 | 8/2012 | |
| WO | 2012/109382 A2 | 8/2012 | |

OTHER PUBLICATIONS

English Translation and Second Office Action for corresponding Chinese Patent Application No. 200980143592.X dated Apr. 21, 2014, 26 pages.
U.S. Appl. No. 14/621,231, filed Feb. 12, 2015 by Bourang et al. (Unpublished.).
U.S. Appl. No. 14/317,387, filed Jun. 27, 2014 by Bourang et al. (Unpublished.).
U.S. Appl. No. 14/294,631, filed Jun. 3, 2014 by Bourang et al. (Unpublished.).
U.S. Appl. No. 14/314,361, filed Jun. 25, 2014 by Bourang et al. (Unpublished.).
U.S. Appl. No. 14/313,742, filed Jun. 24, 2014 by Bourang et al. (Unpublished.).
U.S. Appl. No. 14/321,506, filed Jul. 1, 2014 by Bourang et al. (Unpublished.).
"Drug Delivery Stent With Holes Located on Neutral Axis"; No. 429007; Research Disclosure, Kenneth Mason Publications, Hampshire, CB; Jan. 2000; pp. 13; vol. 2266.
"Stent". Definitions from Dictionary.com. Unabridged (v1.01). Retrieved Sep. 22, 2006, from Dictionary.com, located at http://dictionary.reference.com/search?q=stent; 1 page.
Colombo, "The Invatec Bifurcation Stent Solution" Bifurcation Stents: Novel Solutions, TCT 2003, Washington: Sep. 15-19, 2003, 24 pages.
Cooley, Patrick et al.; "Applications of Ink-Jet Printing Technology to BioMEMs and Microfluidic Systems"; Proceedings, SPIE Conference on Microfluidics and BioMEMs; Oct. 2001; 12 pages.
Evans Analytical Group; "Functional Sites on Non-polymeric Materials: Gas Plasma Treatment and Surface Analysis"; located at http://www.eaglabs.com; 2003; 2 pages.
International Search Report mailed on May 27, 2011, for PCT Patent Application No. PCT/US2011/029863, filed on Mar. 24, 2011, 2 pages.
Joung, Yoon Ki et al.; "Estrogen Release from Metallic Stent Surface for the Prevention of Restenosis"; Journal of Controlled Release; 2003; pp. 83-91; vol. 92.
Lefèvre, Thierry et al. "Approach to Coronary Bifurcation Stenting in 2003"; Euro PCR; May 2003; pp. 127-154.
Stimpson, Donald I. et al; "Parallel Production of Oligonucleotide Arrays Using Membranes and Reagent Jet Printing"; BioTechniques; Nov. 1998; pp. 886-890; vol. 25.
Supplementary European Search Report dated Mar. 25, 2008, for EP Patent Application No. 05727731.1, 2 pages.
Supplementary European Search Report mailed on Apr. 9, 2008, for EP Patent Application No. 05744136.2, 3 pages.
U.S. Appl. No. 09/097,855, filed Jun. 15, 1998, first named inventor: Enrique J. Klein.
U.S. Appl. No. 09/225,364, filed Jan. 4, 1999, first named inventor: Aaron V. Kaplan.
U.S. Appl. No. 10/874,859, filed Jun. 22, 2004, first named inventor: Pablo Acosta.
U.S. Appl. No. 60/336,607, filed Dec. 3, 2001, first named inventor: Bernard Andreas.
U.S. Appl. No. 60/336,767, filed Dec. 3, 2001, first named inventor: Bernard Andreas.
U.S. Appl. No. 60/336,967, filed Dec. 3, 2001, first named inventor: Sunmi Chew.
U.S. Appl. No. 60/364,389, filed Mar. 13, 2002, first named inventor: Sunmi Chew.
U.S. Appl. No. 60/440,839, filed Jan. 17, 2003, first named inventor: Bernard Andreas.
U.S. Appl. No. 60/561,041, filed Apr. 9, 2004, first named inventor: Jeffry Grainger.
U.S. Appl. No. 60/784,309, filed Mar. 20, 2006, first named inventor: Bernard Andreas.
U.S. Appl. No. 60/810,522, filed Jun. 2, 2006, first named inventor: Stephen Kaplan.
U.S. Appl. No. 60/890,703, filed Feb. 20, 2007, first named inventor: Patrick Ruane.
U.S. Appl. No. 61/012,317, filed Dec. 7, 2007, first named inventor: Patrick Ruane.
Written Opinion of the International Searching Authority mailed on May 27, 2011, for PCT Patent Application No. PCT/US2011/029863, filed on Mar. 24, 2011, 11 pages.
First Office Action of Application No. CN 200980143592.X, Jun. 4, 2013, 10 pages.
International Preliminary Report on Patentability of Application No. PCT/US2009/058505, Oct. 28, 2010, 38 pages.
International Search Report and Written Opinion of Application No. PCT/US2009/058505, Nov. 25, 2009, 11 pages.
International Search Report and Written Opinion of Application No. PCT/US2011/029858, May 25, 2011, 10 pages.
International Preliminary Report on Patentability of Application No. PCT/US2011/029859, Sep. 25, 2012, 8 pages.
International Search Report and Written Opinion of Application No. PCT/US2011/029859, May 23, 2011, 8 pages.
International Preliminary Report on Patentability of Application No. PCT/US2011/029861, Sep. 25, 2012, 9 pages.
International Search Report and Written Opinion of Application No. PCT/US2011/029861, May 20, 2011, 11 pages.
International Preliminary Report on Patentability of Application No. PCT/US2011/029862, Sep. 25, 2012, 11 pages.
International Search Report and Written Opinion of Application No. PCT/US2011/029862, May 25, 2011, 13 pages.
International Preliminary Report on Patentability of Application No. PCT/US2011/029863, Sep. 25, 2012, 13 pages.
International Preliminary Report on Patentability of Application No. PCT/US2012/024347, Aug. 13, 2013, 8 pages.
International Search Report and Written Opinion of Application No. PCT/US2012/024347, Jun. 29, 2012, 13 pages.
International Preliminary Report on Patentability of Application No. PCT/US2012/024366, Aug. 13, 2013, 19 pages.
International Search Report and Written Opinion of Application No. PCT/US2012/024366, Sep. 7, 2012, 23 pages.
Invitation to Pay Additional Fees of Application No. PCT/US2012/024366, Jun. 1, 2012, 3 pages.

* cited by examiner

MULTI-STENT AND MULTI-BALLOON APPARATUS FOR TREATING BIFURCATIONS AND METHODS OF USE

CROSS REFERENCE TO RELATED APPLICATION DATA

The present application is a Continuation of PCT/US2012/024366 filed Feb. 8, 2012 (published as WO2012/109382 on Aug. 16, 2012), which application claims the benefit of U.S. Provisional Application No. 61/440,742 filed Feb. 8, 2011; the full disclosures, each of which are incorporated herein by reference in their entirety.

BACKGROUND OF THE INVENTION

Angioplasty and stenting of blood vessels or other body lumens are commonly performed today. Angioplasty is often performed by expanding a balloon in a vessel in order to reduce or eliminate plaque or other blockages. In many cases, a stent is also implanted in the vessel in order to further ensure a positive clinical result. A stent is an implantable scaffold that is typically delivered percutaneously and deployed in a vein, artery, or other tubular body organ for treating an occlusion, stenosis, aneurysm, collapse, dissection, or weakened, diseased, or abnormally dilated vessel or vessel wall. The stent is radially expanded in situ, thereby expanding and/or supporting the vessel wall or body organ wall. In particular, stents are quite commonly implanted in the coronary, cardiac, pulmonary, neurovascular, peripheral vascular, renal, gastrointestinal and reproductive systems. Stents have also been successfully used to reinforce other body parts, such as the urinary tract, the bile duct, the esophagus, the tracheo-bronchial tree and the brain.

Stents may improve angioplasty results by preventing elastic recoil and remodeling of the vessel wall. Stents also can be used to treat dissections in blood vessel walls that are caused by balloon angioplasty. In this situation, the stent is used to appose dissected intimal flaps of tissue which otherwise would extend into and block a vessel.

Conventional stents have also been used to treat more complex vascular problems, such as lesions at or near bifurcation points in the vascular system. A bifurcation is where a secondary artery (sometimes referred to as a side branch or daughter vessel) branches out of a typically larger vessel (sometimes referred to as the main branch or mother vessel). Stenting of bifurcations can present may challenges. For example, a stent that traverses the ostium of the side branch may obstruct blood flow into the side branch. Moreover, the struts in a stent may also block the side branch, limiting or preventing access to the side branch by another diagnostic or therapeutic device such as another catheter. This phenomenon is commonly referred to as "stent jailing." In still other situations, inflation of balloons and expansion of stents in a bifurcation can result in undesirable plaque shifting, which is sometimes referred to as "snow plowing." Other challenges with treatment of a bifurcated vessel can be the result of vessel spasm, dissection, thrombosis, etc.

More recently stents and balloons have also been used to elute drugs locally to the treatment site. Drugs such as rapamycin, everolimus, biolimus A9 and other analogs of rapamycin, as well as paclitaxel are promising in reducing restenosis rates, yet many of the aforementioned challenges of treating a bifurcation still exist.

It would therefore be desirable to provide improved medical devices and methods for treating bifurcated vessels. It would also be desirable to provide improved medical devices and methods that are easier to use, safer, more reliable, and that provide a better clinical outcome compared with currently available medical devices.

Therefore, given the challenges of current stent technology, a need exists for improved stent delivery systems and methods, particularly for treating bifurcated vessels. At least some of these objectives will be met by the present invention.

BRIEF SUMMARY OF THE INVENTION

The present invention relates to methods and delivery systems used to dilate and/or deliver stents in a bifurcated vessel. Embodiments may be configured to stent at least a portion of a mother vessel and a portion of a daughter vessel.

In a first aspect of the present invention, a system for treating a patient's bifurcated vessel having a main branch and a side branch comprises a first delivery catheter and a second delivery catheter. The first delivery catheter carries a first stent which comprises a proximal stent and a distal stent. The first delivery catheter also has a first elongate shaft with a proximal and a distal end. A proximal expandable member has the proximal stent disposed thereover, and a distal expandable member has the distal stent disposed thereover. The proximal and distal expandable members are disposed adjacent the distal end of the first elongate shaft. The proximal and distal expandable members each have a collapsed configuration and a radially expanded configuration. The collapsed configuration has a profile suitable for advancement through a blood vessel, and the expanded configuration has a larger profile than the collapsed configuration profile. The proximal and the distal expandable members are independently expandable of one another.

The second delivery catheter carries a second stent, and also has a second elongate shaft with a proximal and a distal end. A second expandable member with the second stent disposed thereover is disposed adjacent the distal end of the second elongate shaft. The second expandable member has a collapsed configuration and a radially expanded configuration. The collapsed configuration has a profile suitable for advancement through a blood vessel, and the expanded configuration has a larger profile than the profile in the collapsed configuration. The second expandable member is independently expandable of the proximal and the distal expandable members.

In another aspect of the present invention, a system for dilating a bifurcated vessel having a main branch and a side branch in a patient comprises a first delivery catheter and a second delivery catheter. The first delivery catheter has a first elongate shaft with a proximal and a distal end, a proximal expandable member, and a distal expandable member. The proximal and distal expandable members are disposed adjacent the distal end of the first elongate shaft. The proximal and distal expandable members each have a collapsed configuration and a radially expanded configuration. The collapsed configuration has a profile suitable for advancement through a blood vessel, and the expanded configuration has a larger profile than the collapsed configuration profile. The proximal and distal expandable members are independently expandable of one another.

The second delivery catheter has a second elongate shaft with a proximal and a distal end, and a second expandable member. The second expandable member is disposed adjacent the distal end of the second elongate shaft. The second expandable member has a collapsed configuration and a radially expanded configuration. The collapsed configuration has a profile suitable for advancement through a blood vessel, and the expanded configuration has a larger profile than the profile in the collapsed configuration. The second expandable member is independently expandable of the proximal and the distal expandable members.

The first delivery catheter may be adapted to deliver the proximal and distal stents to the main branch adjacent the bifurcation. The second delivery catheter may be adapted to deliver the second stent to the side branch adjacent the bifurcation. A portion of the second delivery catheter may be disposed under a portion of the proximal stent or under a portion of the distal stent, or under a portion of both. The second delivery catheter may be axially slidable relative to the first delivery catheter. The first elongate shaft may comprise a lumen which extends at least partially between proximal and distal ends of the first elongate shaft, and the lumen may be sized to slidably receive the second elongate shaft. The second delivery catheter may be fixed relative to the first delivery catheter so that relative axial movement between the two delivery catheters is prohibited.

Each of the stents may have a collapsed configuration suitable for delivery to the bifurcation, and a radially expanded configuration adapted to engage and support a vessel wall at the bifurcation or adjacent the bifurcation. Each of the stents may be crimped to its respective expandable member so as to prevent ejection of the stent during advancement through a patient's vasculature. A proximal end of the distal stent in the collapsed configuration may abut a distal end of the proximal stent in the collapsed configuration. A proximal end of the distal stent may abut a distal end of the proximal stent so as to form a sidehole in the first stent. The proximal end of the distal stent may comprise a notched region, and the distal end of the proximal stent may also comprise a notched region. The second delivery catheter may slidably pass through the side hole in the first stent. A proximal end of the second stent may comprise a beveled section adapted to fit flush against a sidewall of the proximal stent or a sidewall of the distal stent. A proximal end of the second stent in the radially expanded configuration may be aligned with and abut a side of both the proximal stent in the radially expanded configuration and a side of the distal stent in the radially expanded configuration.

A gap may separate the proximal and the distal expandable members when both the proximal and the distal expandable members are in the collapsed configuration. The gap may be disposed between a proximal end of distal expandable member and a distal end of the proximal expandable member. Expansion of the proximal and the distal members may displace the proximal end of the distal expandable member relative to the distal end of the proximal expandable member so that the proximal end of the distal expandable member advances toward the distal end of the proximal expandable member. This may decrease the gap between the proximal and the distal expandable members. The proximal end of the distal expandable member may abut the distal end of the proximal expandable member when both the proximal and the distal expandable members are in the expanded configuration. The proximal expandable member, the distal expandable member, or the second expandable member may comprise a balloon. A proximal end of the second expandable member may abut a side of both the proximal and the distal expandable members when the proximal, the distal, and the second expandable members are in the radially expanded configuration.

At least one of the first elongate shaft or the second elongate shaft may comprise a guidewire lumen extending at least partially between its proximal and distal ends. The guidewire lumen may be sized to slidably receive a guidewire. The first elongate shaft may comprise a proximal guidewire port and a distal guidewire port adjacent the distal end thereof, and the proximal guidewire port may be closer to the proximal end of the first elongate shaft than the distal end of the first elongate shaft. The proximal guidewire port may be closer to the distal guidewire port than the proximal end of the first elongate shaft. The second elongate shaft may comprise a proximal guidewire port and a distal guidewire port adjacent the distal end thereof, and the proximal guidewire port may be closer to the proximal end of the second elongate shaft than the distal end of the second elongate shaft. The proximal guidewire port may be closer to the distal guidewire port than the proximal end of the second elongate shaft.

In still another aspect of the present invention, a method for treating a bifurcated vessel having a main branch and a side branch in patient comprises providing a first delivery catheter and a second delivery catheter. The first delivery catheter comprises a proximal expandable member, a distal expandable member and a first stent. The proximal and distal expandable members are disposed near a distal end of the first delivery catheter. The first stent comprises a proximal stent and a distal stent. The proximal stent is disposed over the proximal expandable member, and the distal stent is disposed over the distal expandable member. A distal portion of the proximal stent comprises a notched region, and a proximal portion of the distal stent comprises a notched region. The two notched regions are adjacent one another to form a side hole in the first stent.

The second delivery catheter comprises a second expandable member and a second stent. The second expandable member is disposed near a distal end of the second delivery catheter, and the second stent is disposed over the second expandable member. The second delivery catheter passes through the side hole in the first stent. Advancing the first and the second delivery catheter positions the two catheters toward the bifurcation so that the side hole in the first stent may be aligned with the side branch. The second stent is radially expanded from a collapsed configuration to an expanded configuration. The proximal stent is radially expanded from a collapsed configuration to an expanded configuration, and the distal stent is radially expanded from a collapsed configuration to an expanded configuration.

Advancing the first and the second delivery catheters may comprise advancing the first delivery catheter or the second delivery catheter over a guidewire. Aligning the side hole may comprise advancing the first delivery catheter and the second delivery catheter until one or more of the delivery catheters engage a carina of the bifurcation.

Radially expanding the second stent may comprise expanding the second stent to engage a wall of the side branch or a wall of the main branch. Radially expanding the second stent may also comprise expanding the second expandable member. The second expandable member may comprise a balloon, and expanding the second expandable member may comprise inflating the balloon. The second stent may be radially expanded prior to radial expansion of the proximal stent or the distal stent.

Radially expanding the proximal stent may comprise expanding the proximal stent to engage a wall of the main branch. Radially expanding the proximal stent may also comprise expanding the proximal expandable member. The proximal expandable member may comprise a balloon, and expanding the proximal expandable member may comprise inflating the balloon. The proximal stent may be radially expanded before radial expansion of the distal stent.

Radially expanding the distal stent may comprise expanding the distal stent to engage a wall of the main branch or a wall of the side branch. Radially expanding the distal stent may also comprise expanding the distal expandable member. The distal expandable member may comprise a balloon, and expanding the distal expandable member may comprise inflating the balloon.

The method may further comprise proximally retracting the second delivery catheter so that a proximal end of the second stent is aligned with the side hole in the first stent. A proximal end of the second stent may be aligned with an ostium of the side branch. Proximally retracting the second delivery catheter may comprise aligning a radiopaque maker on the second delivery catheter with a radiopaque marker on the first delivery catheter. Proximally retracting the second delivery catheter may comprise sliding the second delivery catheter under a portion of the first stent. The second delivery catheter may slide under a portion of the proximal stent or under a portion of the distal stent. Proximally retracting the second delivery catheter may comprise sliding the second delivery catheter through the side hole in the first stent. A proximal portion of the second stent may abut both a distal portion of the proximal stent and a proximal portion of the distal stent after radial expansion of the proximal stent, the distal stent, and the second stent. The distal portion of the proximal stent may abut the proximal portion of the distal stent after radial expansion of the stents.

In still another aspect of the present invention, a method for treating a bifurcated vessel having a main branch and a side branch in a patient comprises providing a first delivery catheter and a second delivery catheter. The first delivery catheter comprises a proximal expandable member, a distal expandable member and a first stent. The proximal and distal expandable members are disposed near a distal end of the first delivery catheter. The first stent comprises a proximal stent and a distal stent. The proximal stent is disposed over the proximal expandable member, and the distal stent is disposed over the distal expandable member. A distal portion of the proximal stent comprises a notched region, and a proximal portion of the distal stent comprises a notched region. The notched regions are adjacent one another to form a side hole in the first stent.

The second delivery catheter comprises a second expandable member and a second stent. The second expandable member is disposed near a distal end of the second delivery catheter, and the second stent is disposed over the second expandable member. The second delivery catheter passes through the side hole in the first stent. Advancing the first and second delivery catheters positions them toward the bifurcation. The first stent and the second stent are positioned at the bifurcation such that the proximal stent is disposed in the main branch, the distal stent is disposed in the side branch, and the second stent is disposed in the main branch downstream of the bifurcation. The side hole in the first stent is aligned with the main branch and faces downstream of the bifurcation. The distal stent is radially expanded from a collapsed configuration to an expanded configuration. The proximal stent is radially expanded from a collapsed configuration to an expanded configuration. The second stent is radially expanded from a collapsed configuration to an expanded configuration.

In yet another aspect of the present invention, a method for treating a bifurcated vessel having a main branch and a side branch in a patient comprises providing a first delivery catheter and a second delivery catheter. The first delivery catheter comprises a proximal expandable member and a distal expandable member. The proximal and distal expandable members are disposed near a distal end of the first delivery catheter, and the expandable members are independently expandable from one another. The second delivery catheter comprises a second expandable member disposed near a distal end thereof. The first and second delivery catheters are advanced toward the bifurcation and the second expandable member is positioned in the side branch. The proximal and distal expandable members are positioned in the main branch so that the proximal expandable member is at least partially upstream of the bifurcation, and the distal expandable member is at least partially downstream of the bifurcation. The second expandable member is radially expanded from a collapsed configuration to an expanded configuration. The proximal expandable member is radially expanded from a collapsed configuration to an expanded configuration. The distal expandable member is radially expanded from a collapsed configuration to an expanded configuration.

Radially expanding the second expandable member may comprise expanding the second expandable member into engagement with a wall of the side branch or the main branch. The second expandable member may comprise a balloon, and expanding the second expandable member may comprise inflating the balloon. The second expandable member may be expanded prior to radial expansion of the proximal expandable member or the distal expandable member.

Radially expanding the proximal expandable member may comprise expanding the proximal expandable member to engage a wall of the main branch. The proximal expandable member may comprise a balloon, and expanding the expandable member may comprise inflating the balloon. The proximal expandable member may be expanded before radial expansion of the distal expandable member, or before expansion of the second expandable member. The proximal expandable member may also be expanded simultaneously with the distal expandable member, the second expandable member, or simultaneously with both.

Radially expanding the distal expandable member may comprise expanding the distal expandable member to engage a wall of the main branch or the side branch. The distal expandable member may comprise a balloon, and expanding the distal expandable member may comprise inflating the balloon. The distal expandable member may be expanded before expansion of the proximal expandable member or second expandable member.

The method may further comprise proximally retracting the second delivery catheter so that a proximal end of the second expandable member is aligned with an ostium of the side branch. Proximally retracting the second delivery catheter may comprise sliding the second delivery catheter under a portion of the proximal expandable member. Both the proximal and distal expandable members may be radially expanded simultaneously. A proximal portion of the distal expandable member may engage a distal portion of the proximal expandable member.

In still another aspect of the present invention, a method for treating a bifurcated vessel having a main branch and a side branch in a patient comprises providing a first delivery catheter and a second delivery catheter. The first delivery catheter comprises a proximal expandable member and a distal expandable member. The proximal and distal expandable members are disposed near a distal end of the first delivery catheter. The proximal and the distal expandable members are independently expandable from one another. The second delivery catheter comprises a second expandable member disposed near a distal end thereof. The first and second delivery catheters are advanced toward the bifurcation, and the proximal expandable member is positioned in the main branch adjacent the bifurcation. The distal expandable member is positioned in the side branch adjacent the bifurcation. The second expandable member is positioned in the main branch downstream of the proximal expandable member. The distal expandable member is radially expanded from a collapsed configuration to an expanded configuration. The proximal expandable member is radially expanded from a collapsed configuration to an expanded configuration. The second expandable member is radially expanded from a collapsed configuration to an expanded configuration.

In yet another aspect of the present invention, a system for treating a patient with a trifurcated vessel having a main branch, a first side branch, and a second side branch comprises a first delivery catheter, a second delivery catheter and a third delivery catheter. The first delivery catheter carries a first stent. The first stent comprises a proximal stent and a distal stent. The first delivery catheter also has a proximal elongate shaft with a proximal and a distal end, and a distal elongate shaft with a proximal and distal end. The proximal elongate shaft comprises a proximal expandable member with the proximal stent disposed thereover, and the distal elongate shaft comprises a distal expandable member with the distal stent disposed thereover. The proximal and distal expandable members are disposed adjacent the distal end of the first delivery catheter. The proximal and distal expandable members each have a collapsed configuration and a radially expanded configuration. The collapsed configuration has a profile suitable for advancement through a blood vessel, and the expanded configuration has a larger profile than the collapsed configuration profile. The proximal and distal expandable members are independently expandable of one another. The second delivery catheter carries a second stent, and also has a second elongate shaft with a proximal and a distal end, and a second expandable member with the second stent disposed thereover. The second expandable member is disposed adjacent the distal end of the second elongate shaft. The second expandable member has a collapsed configuration and a radially expanded configuration. The collapsed configuration has a profile suitable for advancement through a blood vessel, and the expanded configuration has a larger profile than the profile in the collapsed configuration. The second expandable member is independently expandable of the proximal and the distal expandable members. The third delivery catheter carries a third stent. The third delivery catheter also has a third elongate shaft with a proximal and a distal end, and a third expandable member with the third stent disposed thereover. The third expandable member is disposed adjacent the distal end of the third elongate shaft. The third expandable member has a collapsed configuration and a radially expanded configuration. The collapsed configuration has a profile suitable for advancement through a blood vessel, and the expanded configuration has a larger profile than the profile in the collapsed configuration. The third expandable member is independently expandable of the second expandable member, and the proximal and the distal expandable members.

These and other embodiments are described in further detail in the following description related to the appended drawing figures.

DETAILED DESCRIPTION OF THE INVENTION

The present invention relates to medical devices and methods, and more particularly to stent and dilatation delivery systems for treating bifurcated vessels having a main branch and a side branch. However, this is not intended to be limiting, and one of skill in the art will appreciate that the devices and methods described herein may be used to treat other regions of the body.

The scientific community is slowly moving away from a main branch vs. side branch model and nomenclature. It is now well accepted that a "mother" vessel bifurcates into two "daughter vessels," that are anatomically after the carina. The vessel that appears to be the continuation of the mother vessel is usually less angulated. The other vessel may be commonly referred to as the side branch, or a daughter vessel. Therefore, in this specification, the terms "main branch," "trunk," or "mother vessel" may be used interchangeably. Also in this specification, the terms "side branch vessel" and "daughter vessel" may also be used interchangeably. The terms "main branch stent," "trunk stent," or "mother stent" are interchangeable, and the term "side branch stent" is also interchangeable with the term "daughter stent." In the case where a main branch vessel bifurcates into two equally sized branches, one of the branches may still be considered to be the main branch or mother vessel, and the other branch may be considered a side branch or daughter vessel.

Systems for Treating a Bifurcation

Figure 1:
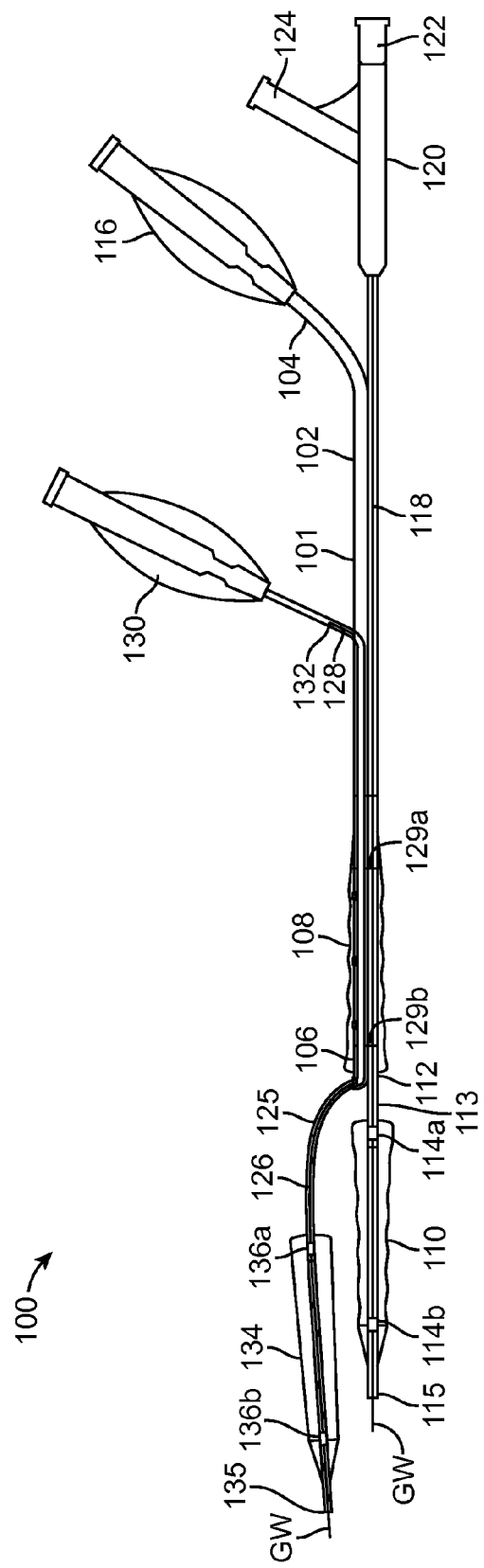
FIG. 1 illustrates an exemplary embodiment of a system for treating a bifurcation.

Referring now to FIG. 1, a system 100 for treating bifurcations comprises a first catheter 101 and a second catheter 125. The first catheter includes a first elongate shaft 102 having a proximal region 104 and a distal region 112. A proximal expandable member, here a balloon 108, and a distal expandable member, also a balloon 110 are disposed near the distal region of the first catheter 101. A gap 113 separates the proximal expandable member 108 from the distal expandable member 110. The proximal expandable member is disposed on the first elongate shaft 102, and the distal expandable member 110 is disposed over an extended portion 112 of the first shaft 102. The extended portion 112 may be a stepped down, reduced diameter portion of the first shaft 102, or it may be a separate shaft that is coupled with the first shaft 102. The extended portion may also be a coextruded shaft that extends parallel to the first shaft. The extended portion 112 may be fixed relative to the first shaft 102, or it may also be slidably movable relative to the first shaft 102. Proximal 114a and distal 114b radiopaque markers may be disposed adjacent the distal expandable member 110 in order to allow a physician to visualize balloon location during fluoroscopy. Similarly, proximal 129*a* and distal 129*b* radiopaque markers may be disposed adjacent the proximal balloon 108. The markers are preferably positioned at the proximal and distal working ends of the respective balloon. An inflation lumen (not illustrated) allows the balloon 110 to be inflated from the proximal end of the first catheter. A guidewire lumen 118 extends from a distal port 115 at the distal end of the extension shaft to the proximal portion of the catheter and terminates in a Y-connector 120 having two ports 122, 124 with fittings such as Luer fittings. The Luer fittings may be used to fluidly couple the catheter with a balloon inflation device such as an Indeflator, a syringe, medical tubing, or other devices commonly used during a catheterization procedure. The guidewire lumen 118 is coupled with port 122, and thus the first catheter may be delivered over a guidewire GW which slidably passes from the distal port 115, through the extended portion 112, though the first catheter 102, and exits proximal port 122. This configuration is commonly referred to as an over-the-wire configuration. While not illustrated, one of skill in the art will also appreciate that the proximal guidewire port may also be located anywhere along the first delivery catheter, and in some preferred embodiments the proximal port 122 is located closer to the distal port 115 than the proximal end of the first catheter. This configuration is commonly referred to as Rx, or rapid exchange configuration. Both balloons may be inflated independently of one another, and thus balloon 108 has its own inflation lumen (not illustrated) which is passes through the first elongate shaft 102 and terminates at hub 116 which has a fitting such a Luer fitting to allow an inflation device such as an Indeflator to be fluidly coupled to the catheter. Both the proximal and distal expandable members may be expanded from a collapsed configuration having a low profile suitable for intravascular delivery to a target treatment site such as a bifurcated vessel, to a radially expanded configuration in which the balloons engage the walls of the target treatment site, such as a blood vessel wall.

The second catheter 125 also has an elongate shaft 126 having a proximal portion and a distal portion. An expandable member 134, here a balloon, is disposed on the elongate shaft 126, near it's distal end. A proximal 136*a* and distal 136*b* radiopaque marker may be coupled to the shaft 126 and aligned with the balloon 134 so that a physician may visualize the balloon under fluoroscopy. The radiopaque markers 136*a*, 136*b* are preferably located at the proximal and the distal working ends of the balloon 134. A proximal connector 130 is coupled to the proximal end of the shaft 126 and allows a syringe, inflation device, medical tubing, or other device to be fluidly coupled with an inflation lumen (not shown) which extends along the elongate shaft 126 and is fluidly coupled to the expandable member 134. A guidewire lumen 128 extends from a distal port 135 to a proximal port 132. In preferred embodiments, the proximal port 132 is closer to the distal port 135 than the proximal end of the elongate shaft 126. This configuration is often referred to as Rx or rapid exchange. The guidewire lumen may also optionally extend out the proximal end of the shaft to provide a catheter having what is commonly referred to as an over-the-wire configuration. In preferred embodiments, shaft 126 may extend slidably through a lumen 106 in the shaft 102 of the first catheter 101 so that the balloon 134 may be advanced or retracted relative to the distal balloon 110. In other embodiments, shaft 126 may be fixedly attached to shaft 102 with no relative movement between the two catheters. Balloon 134 may be expanded from a collapsed configuration having a low profile suitable for intravascular delivery to a target treatment site such as a bifurcated vessel, to a radially expanded configuration in which the balloons engage the walls of the target treatment site, such as a blood vessel wall. Any of the balloons 108, 110, 134 may be compliant, non-compliant, or semi-compliant. Moreover, any of the balloons 108, 110, 134 may have a substantially constant diameter, or they may be tapered to match the contours of a vessel. In preferred embodiments, the balloons are tapered and non-compliant.

Figure 2:
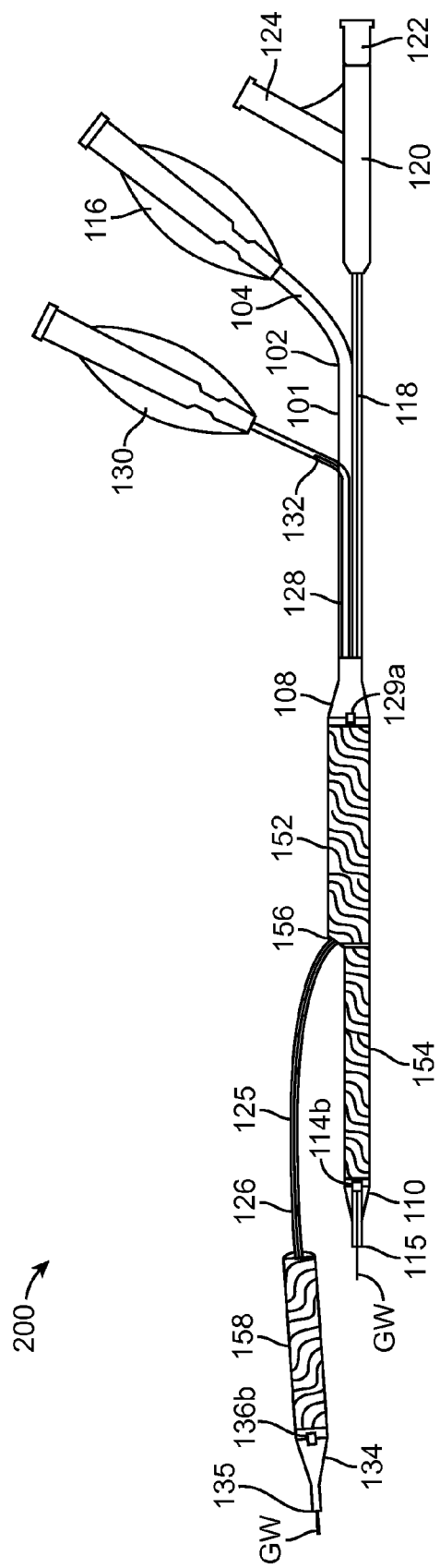
FIG. 2 illustrates an exemplary embodiment of a stent delivery system for treating a bifurcation.

FIG. 2 illustrates another catheter system 200 for treating a bifurcation. In this exemplary embodiment, catheter system 200 is similar to the system 100 of FIG. 1, with the major difference being that system 100 also includes three stents 152, 154, 158.

The first catheter carries a first stent which is comprised of two discrete stents, a proximal stent 152 is disposed over the proximal balloon 108 on the first catheter 101, and a distal stent 154 is disposed over the distal balloon 110. A proximal end of the distal stent 154 abuts with a distal end of the proximal stent 108. The abutting ends of the two stents are formed so that when the two stents abut one another, a side hole 156 is created, allowing the second elongate shaft 126 to pass therethrough. Exemplary embodiments of the stent side hole are disclosed in greater detail below. The side hole 156 is preferably disposed about midway between the proximal and distal stents 152, 154, however, by changing stent lengths or by further modifying the abutting ends of the stents, the side hole may be disposed anywhere between the ends of the two stents 152, 154. A second stent 158, comprised of a single stent is disposed over balloon 134 on the second delivery catheter. Other aspects of delivery system 200 generally take the same form as those previously described above with respect to catheter system 100. The stents 152, 154, 158 are preferably balloon expandable, but may also be self-expanding, or combinations of balloon expandable and self-expanding. The stents 152, 154, 158 are radially expandable from a collapsed or crimped configuration having a profile adapted for intravascular delivery through a vessel, to an expanded configuration in which the stents engage and provide support for a target tissue such as a vessel wall. The stents may have any length, and in preferred embodiments, the proximal stent 152, and the distal stent 154 are substantially the same length. One of skill in the art will appreciate that this is not intended to be limiting, and stent length is dependent upon the length of the target tissue being treated.

Figure 3A:
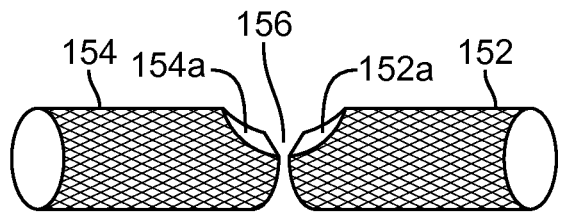
FIG. 3A illustrates a perspective view of two notched stents that form a side hole.
Figure 3B:
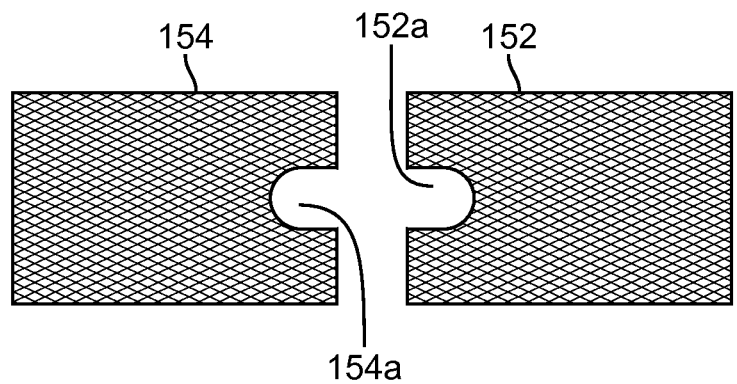
FIG. 3B illustrates a flat, unrolled view of the stents in FIG. 3A.
Figure 3C:
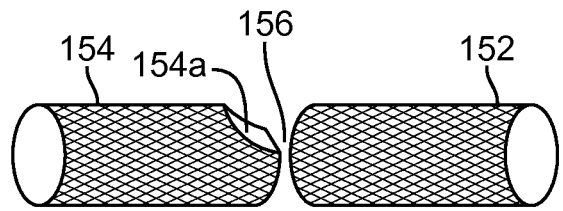
FIG. 3C illustrates a perspective view of a side hole formed by notching one stent in a pair of adjacent stents.

FIG. 3A illustrates a perspective view of the two stents 152, 154 in FIG. 2, with the delivery catheter removed for clarity. A proximal portion of distal stent 154 includes a notched region 154*a*, and similarly a distal portion of the proximal stent 152 also includes a notched portion 152*a*. The notched regions may be sized so that when the proximal portion of stent 154 abuts with the distal portion of stent 152, the two notched regions form a side hole 156 through which the second catheter 126 may pass. FIG. 3B illustrates the stents 152, 154 in the unrolled, flattened configuration to more clearly illustrate how the notched region may be cut into the stent. In this exemplary embodiment, the notched region is half of an ellipse, but in other embodiments, the notched region may be circular, rectangular, or other shapes may be employed. Also, in still other embodiments, the notch may be cut out of only one of the two abutting stents. FIG. 3C illustrates an exemplary embodiment of two stents 152, 154 that form a side hole 156 when the two stents abut one another. In this embodiment, a single notch 154*a* is cut out of only one of the stents, here stent 154 in this embodiment, although the notch could also be cut out of stent 152.

Figure 3D:
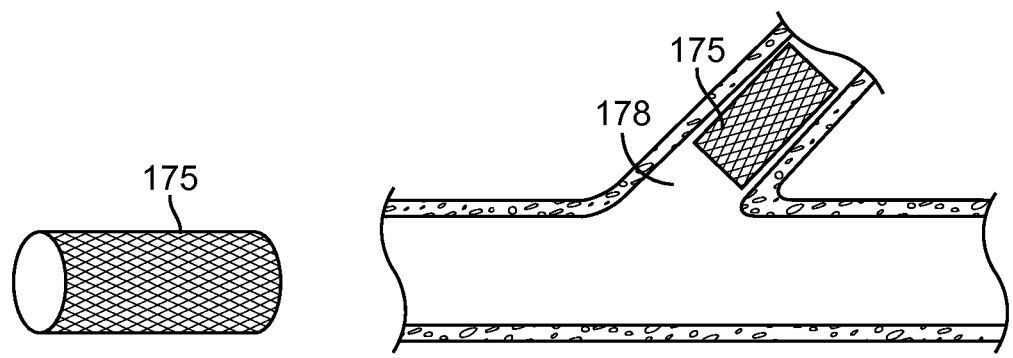
FIGS. 3D-3E illustrate how various stent geometries may conform to a bifurcated vessel.
Figure 3E:
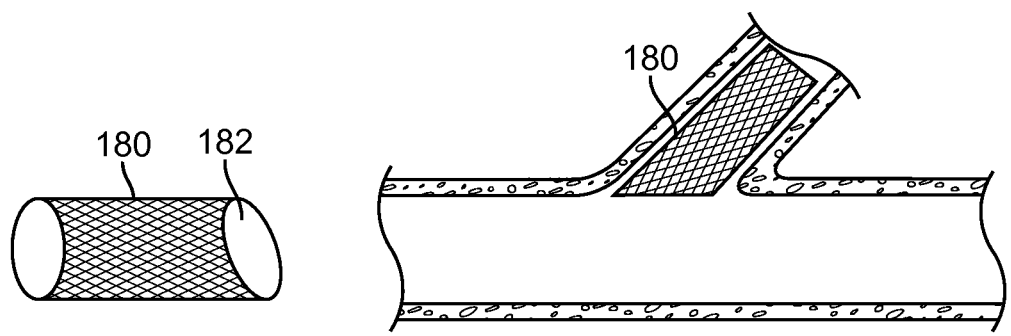

For conventional cylindrical stents 175 having orthogonal ends, placement in a side branch may result in a region 178 of the side branch that is remains unscaffolded, as seen in FIG. 3D. Providing a stent 180 having a beveled end 182 may allow the stent to more accurately conform to the side branch anatomy, thereby providing more uniform scaffolding as seen in FIG. 3E.

Methods of Treating a Bifurcation

Figure 4A:
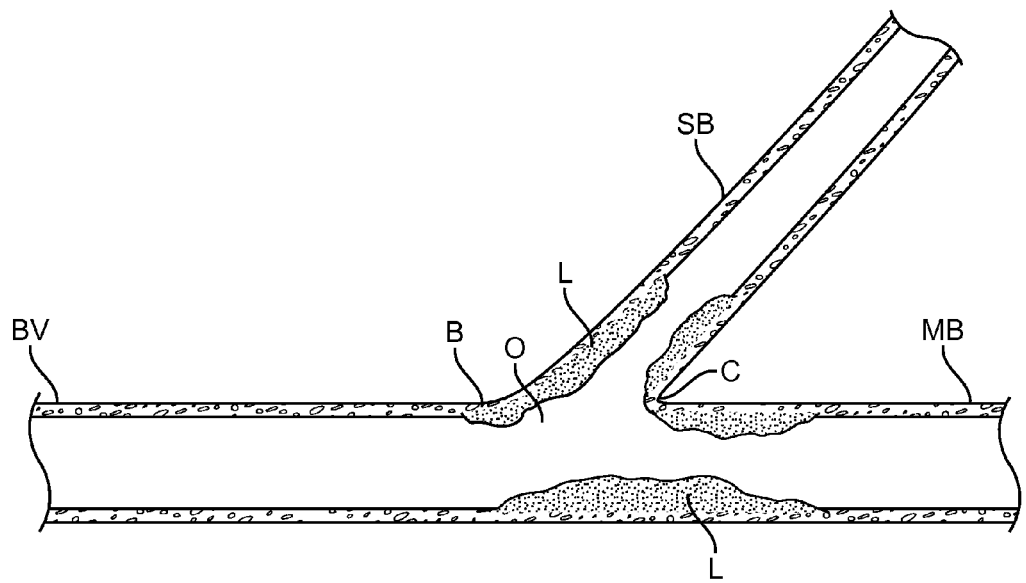
FIGS. 4A-4J illustrate an exemplary method of treating a bifurcation.

FIGS. 4A-4J illustrate an exemplary method of treating a bifurcated vessel using the system 100 of FIG. 1. FIG. 4A illustrates the basic anatomy of stenotic lesion at a bifurcated vessel. The blood vessel BV includes a main branch MB and a side branch SB. At the bifurcation B, the vessel bifurcates into the side branch SB and a downstream portion of the main branch MB. The carina C is a keel-shaped ridge, process, or anatomical part of the bifurcation. A stenotic lesion L such as plaque, calcified deposits, or other narrowing material is disposed in the side branch, as well as in the main branch upstream and downstream of the bifurcation. The ostium O is the opening from the main branch MB into the side branch SB.

Figure 4B:
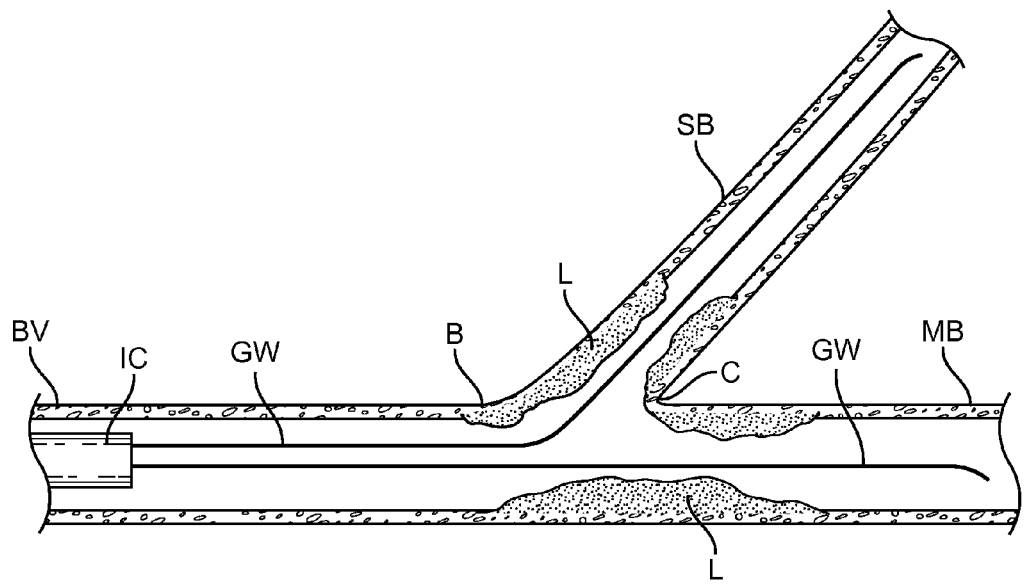

In FIG. 4B a guidecatheter or introducer catheter IC is introduced into the patient's vasculature, preferably percutaneously, or via cutdown. The introducer catheter IC is then advanced toward the target treatment area at the bifurcation. Two guidewires GW are then advanced through the introducer catheter. One guidewire is further advanced into the side branch SB past the side branch lesion L, and the other guidewire is advanced further into the main branch downstream of the main branch lesion L.

Figure 4C:
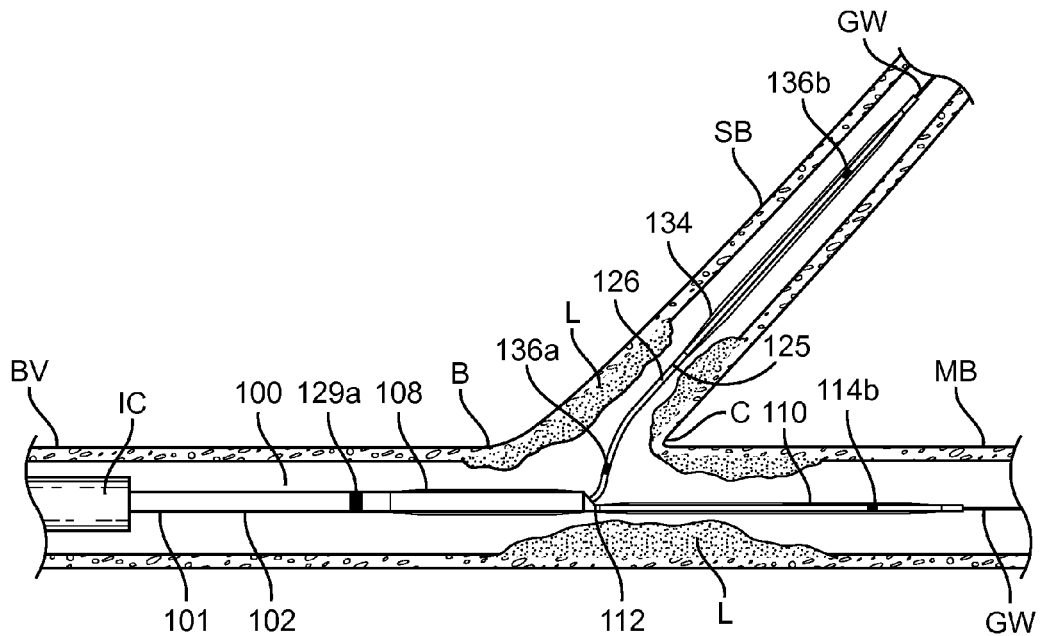

FIG. 4C shows the bifurcation treatment system 100 of FIG. 1 being advanced through the introducer catheter IC, over both guidewires GW. Both catheters 101, 125 are advanced distally until they engage the carina C, resisting further distal advancement. Both catheters may be advanced slightly distally, or retracted slightly proximally such that the first catheter 101 is positioned in the main branch MB with the proximal balloon 108 at least partially upstream of the bifurcation B, and the distal balloon 110 is at least partially downstream of the bifurcation B. Both balloons 108, 110 of course will be aligned with the lesion L in the main branch MB. The second catheter 125 is positioned in the side branch SB, preferably such that balloon 134 is slightly distal to the side branch lesion L.

Figure 4D:
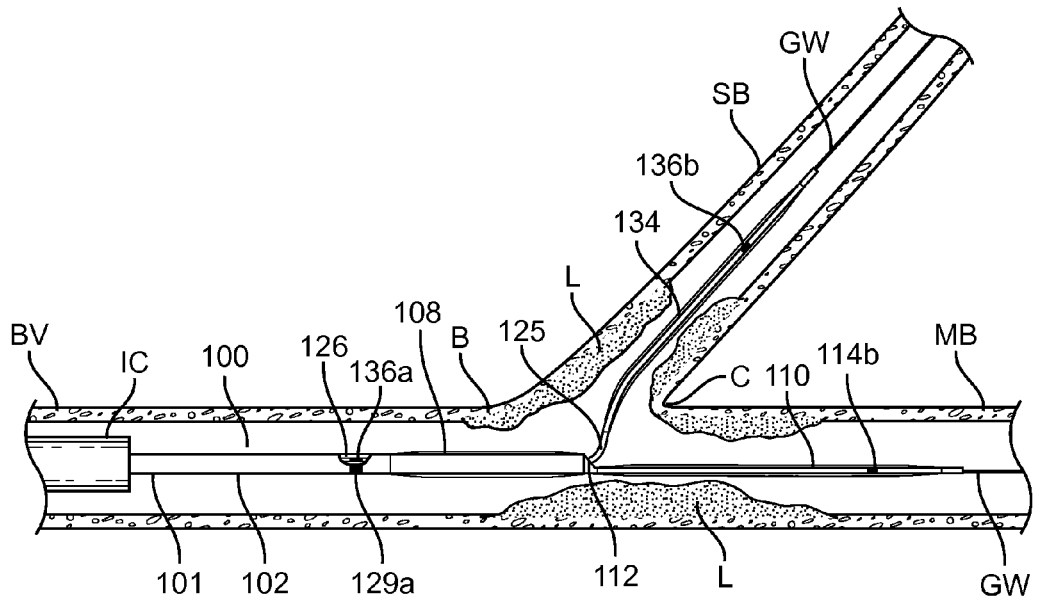

FIG. 4D illustrates an optional step wherein the second catheter 125 is proximally retracted through a lumen (not shown) in the first catheter 101 so that proximal radiopaque marker 136a on the second catheter 125 is aligned with proximal radiopaque marker 129a on the first catheter 101. This may be seen in the partial cutaway in FIG. 4D. Thus, a portion of shaft 126 slides under proximal balloon 108 and through the shaft 102 of the first catheter 101. Furthermore, this ensures alignment of balloon 134 with the side branch lesion L, with the ostium of the side branch, and with the proximal 108 and distal 110 balloons. This aspect of the procedure, as well as any other aspect of the procedure may be visualized using fluoroscopy, ultrasound, or other imaging techniques suitable for catheterization procedures.

Figure 4E:
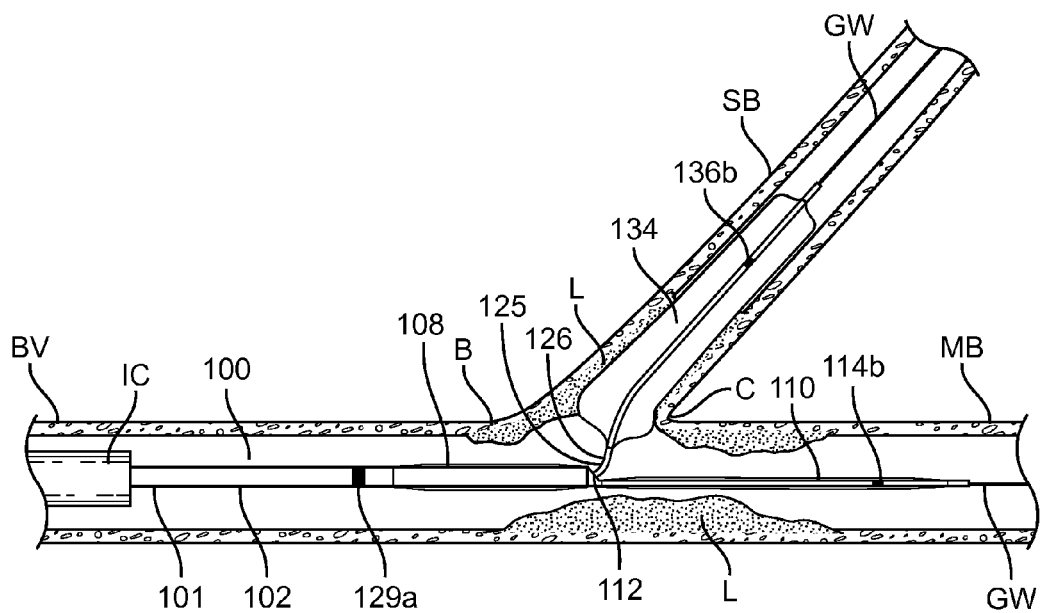

Once the balloons on both catheters are properly aligned with the lesion, the bifurcation, and with one another, the balloons may be radially expanded in any order in order to treat the lesion L. FIG. 4E illustrates a preferred first inflation wherein the balloon 134 on the second catheter 125 is expanded against the lesion L in the side branch SB. The balloon 134 may be inflated with saline, contrast media, combinations thereof, or with other fluids. The balloons are inflated to a pressure high enough to compact the plaque into the vessel wall, preferably greater than 10 atmospheres, more preferably 10 to 20 atmospheres, and even more preferably 15 to 25 atmospheres. Of course, one of skill in the art will appreciate that this pressure is not limiting, and a physician may inflate the balloon to any desired pressure. After the balloon is inflated once, or twice, or more, it is deflated, and the plaque will be substantially reduced since it is pressed into the vessel wall, thereby reducing the stenotic lesion L.

Figure 4F:
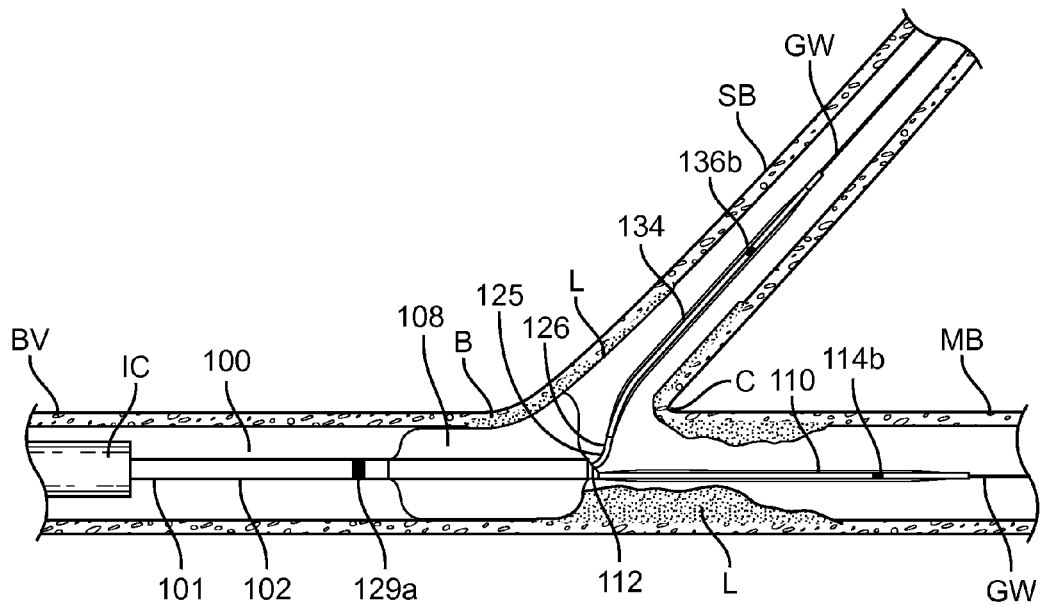
Figure 4G:
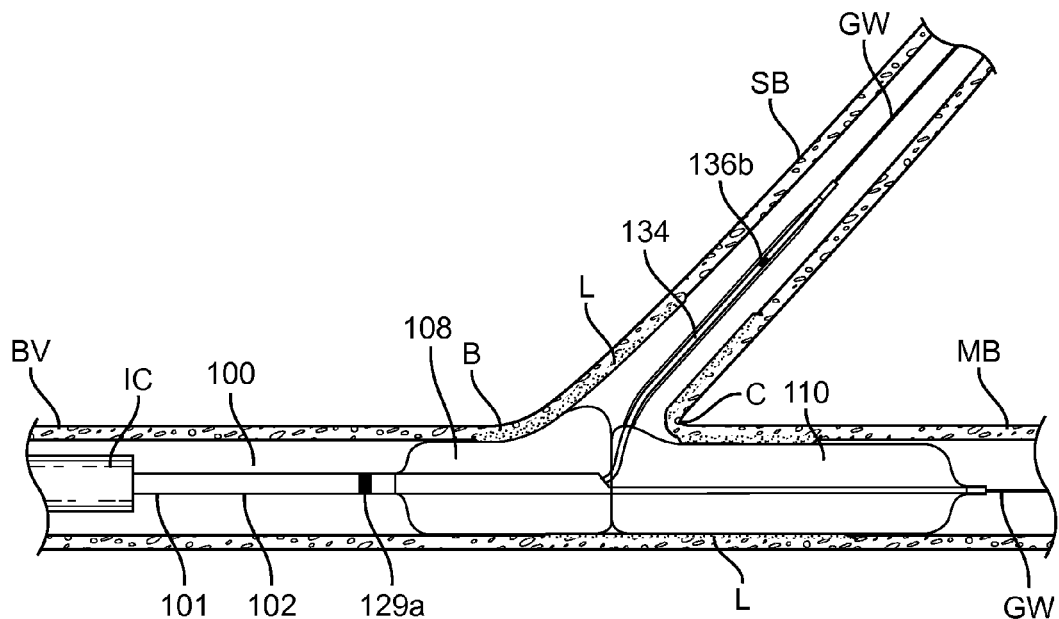

FIG. 4F illustrates another preferred step, wherein the proximal balloon 108 is expanded next, after expansion of the balloon 134 in the side branch SB. The proximal balloon may be inflated with similar fluids and pressures as previously described above. This reduces the plaque in the main branch near the bifurcation, and upstream of the bifurcation. FIG. 4G illustrates the next preferred step wherein the distal balloon 110 is expanded using similar fluids and pressures as described above. Expansion of both proximal 108 and distal 110 balloons is a modified "kissing" balloon technique. Even though the balloons 108, 110 are separated by a gap, after inflation, the proximal end of the distal balloon 110 expands toward and abuts the distal end of the proximal balloon 108 which also advances toward the other balloon. Additional details on this are disclosed below in FIGS. 8 and 9A-9B. Expanding both the proximal and distal balloons 108, 110 ensures that the lesion L in the main branch, both upstream and downstream of the bifurcation is uniformly dilated. Optionally, the side branch balloon 134 may also be simultaneously expanded (not illustrated) so that all three balloons "kiss" one another.

Figure 4H:
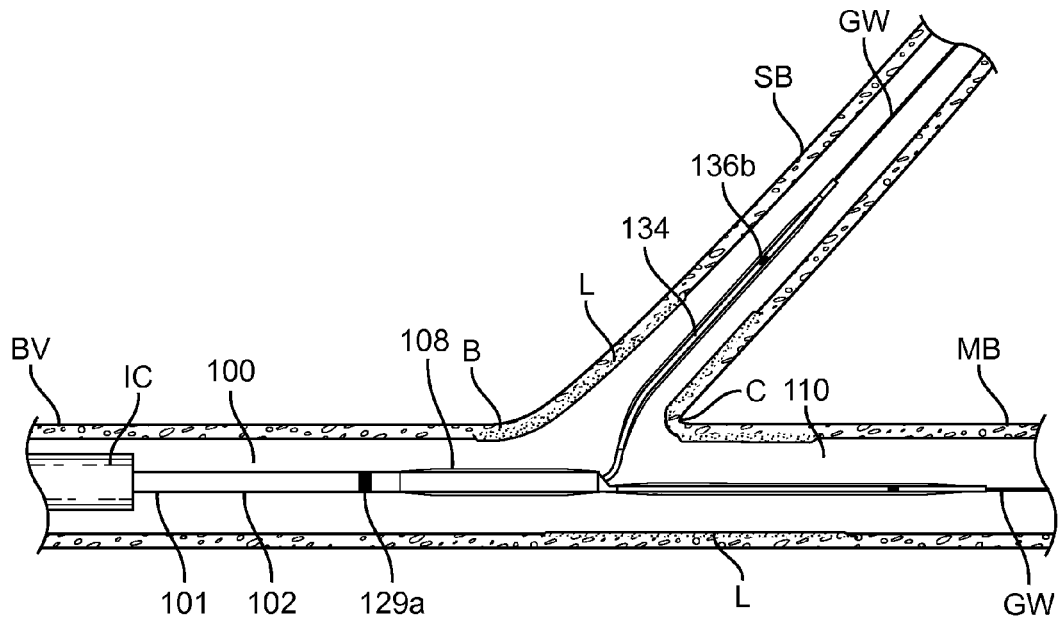
Figure 4I:
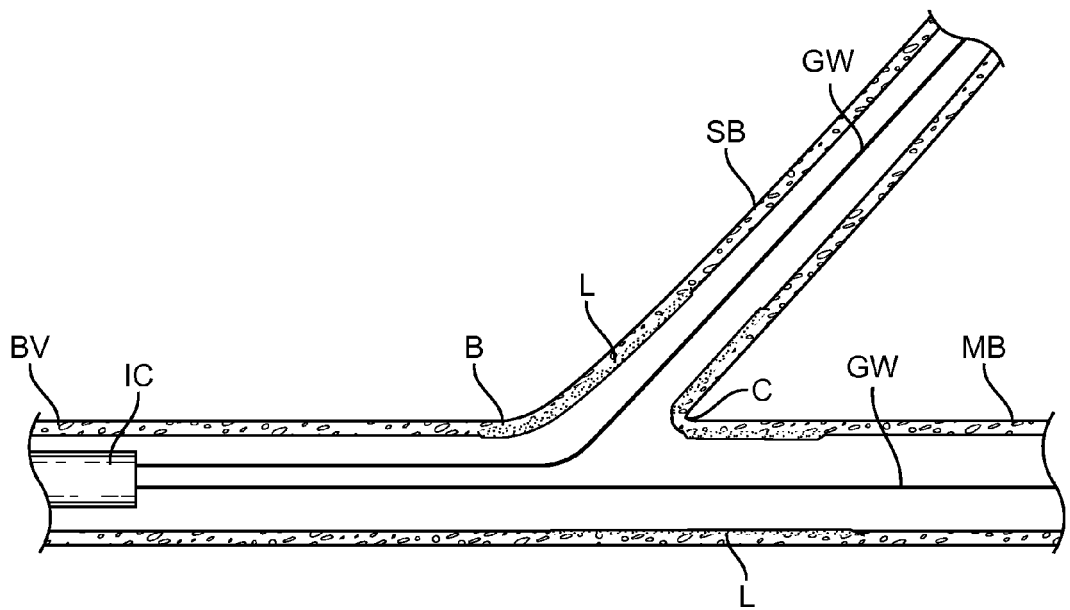
Figure 4J:
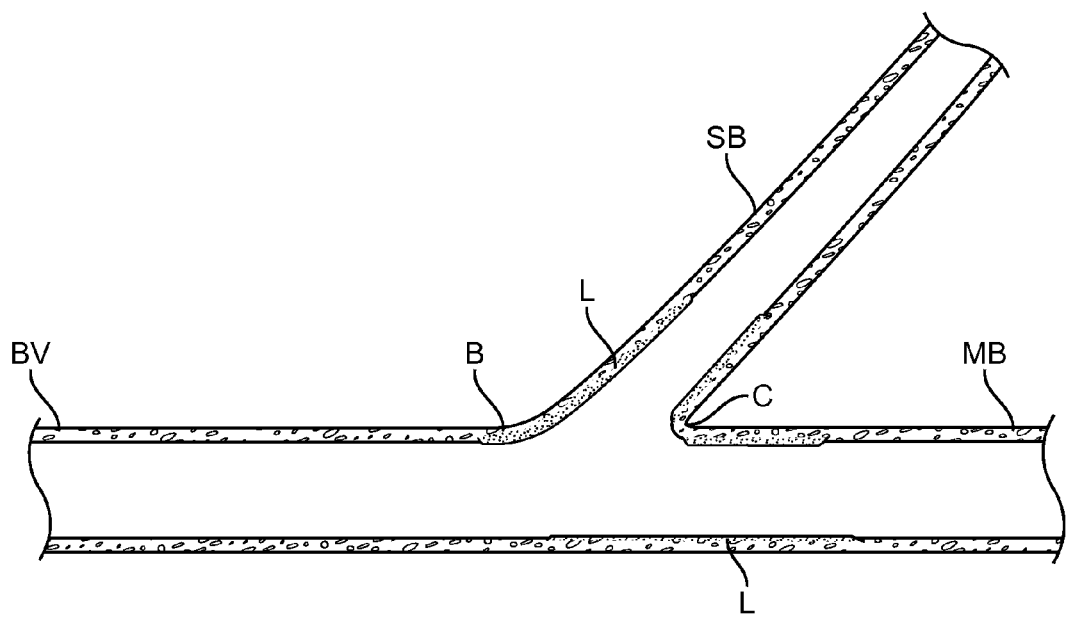

After the lesion has been successfully dilated, both proximal and distal balloons 108, 110 (and side branch balloon 134, if also expanded) are deflated as illustrated in FIG. 4H. In FIG. 4I, both catheters 101, 125 are proximally retracted away from the bifurcation, and removed from the patient's body. Finally, in FIG. 4J, both guidewires GW and the introducer guidecatheter IC are also proximally retracted away from the bifurcation and removed from the patient's body. The blockage in the lumen is now substantially reduced, thereby improving blood flow across the bifurcation.

The exemplary method described above is not intended to be limiting. One of skill in the art will appreciate that a number of variations or changes may also be made. For example, any one or more of the balloons may be coated with a therapeutic agent such as an anti-restonois drug like rapamycin, everolimus, biolimus A9, other analogs of rapamycin, or paclitaxel to help reduce restenosis. Moreover, any order or combination of balloon inflation may also be used. For example, the proximal and distal balloons may be expanded prior to expansion of the side branch balloon, or the distal balloon maybe inflated before the proximal balloon. Other variations may include simultaneous inflation of the side branch balloon with the proximal balloon, or simultaneous inflation of the side branch balloon and the distal balloon. Any number of permutations are contemplated.

Figure 5:
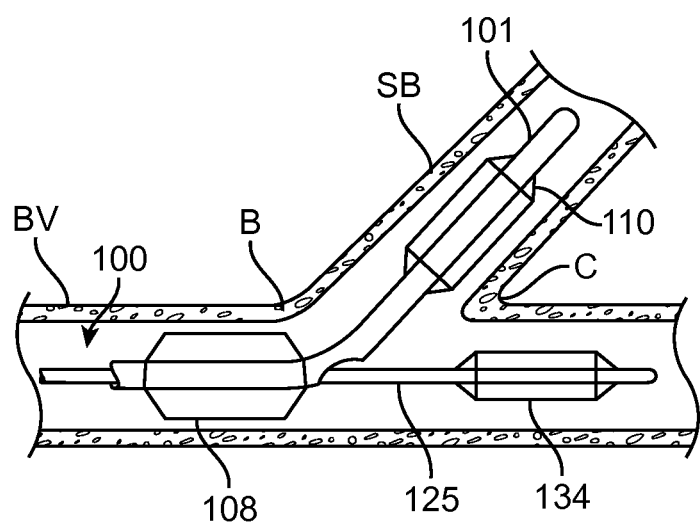
FIG. 5 illustrates another exemplary method of treating a bifurcation.

Additionally, in an alternative embodiment shown in FIG. 5, the distal balloon 110 of the first catheter 101 may be advanced into the side branch SB while the proximal balloon 108 remains in the main branch MB. The balloon 134 on the second catheter 125 may then be advanced into the main MB branch at least partially downstream of the bifurcation. Inflation of the balloons may follow any of the number of permutations discussed above.

Figure 6A:
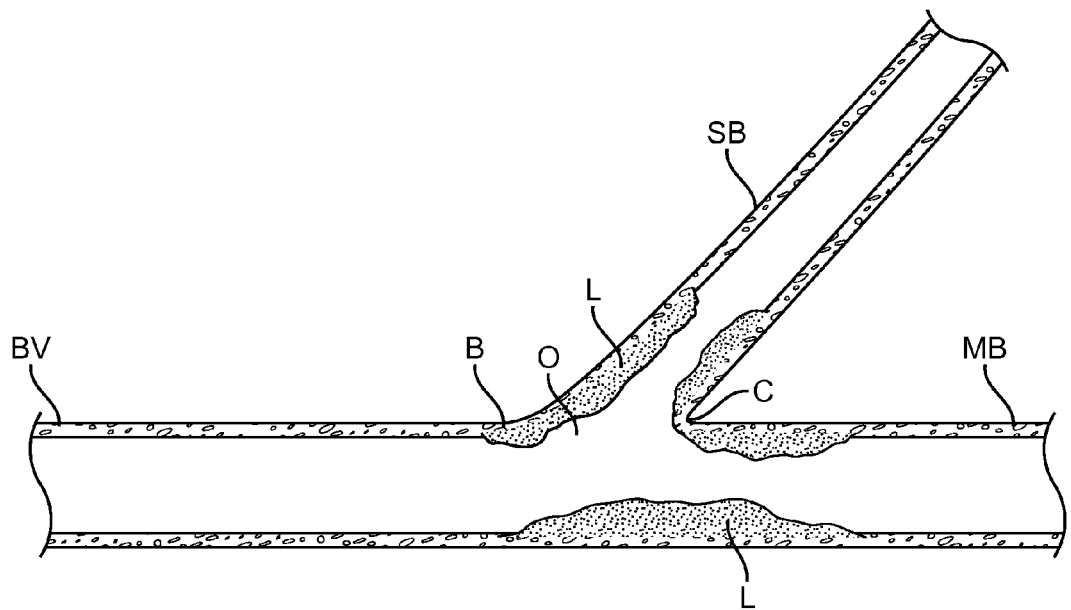
FIGS. 6A-6J illustrate an exemplary method of stenting a bifurcation.

FIGS. 6A-6J illustrate an exemplary method of stenting a bifurcation using the delivery system 200 previously described in FIG. 2 above. FIG. 6A illustrates the basic anatomy of stenotic lesion at a bifurcated vessel. The blood vessel BV includes a main branch MB and a side branch SB. At the bifurcation B, the vessel bifurcates into the side branch SB and a downstream portion of the main branch MB. The carina C is a keel-shaped ridge, process, or anatomical part of the bifurcation. A stenotic lesion L such as plaque, calcified deposits, or other narrowing material is disposed in the side branch, as well as in the main branch upstream and downstream of the bifurcation. The ostium O is the opening from the main branch MB into the side branch SB.

Figure 6B:
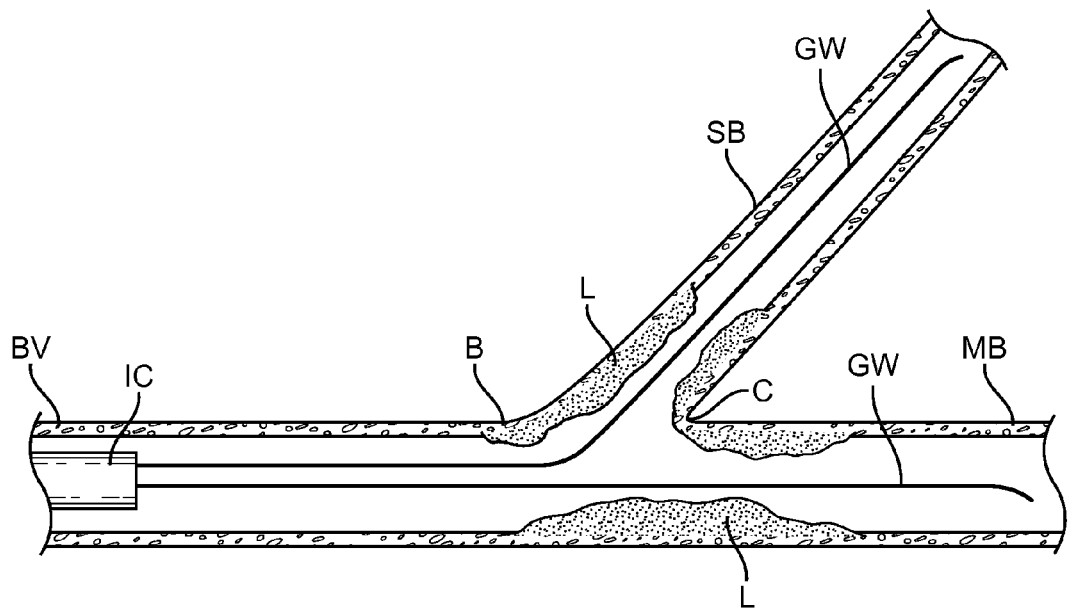

In FIG. 6B a guidecatheter or introducer catheter IC is introduced into the patient's vasculature, preferably percutaneously, or via cutdown. The introducer catheter IC is then advanced toward the target treatment area at the bifurcation. Two guidewires GW are then advanced through the introducer catheter. One guidewire is further advanced into the side branch SB past the side branch lesion L, and the other guidewire is advanced further into the main branch downstream of the main branch lesion L.

Figure 6C:
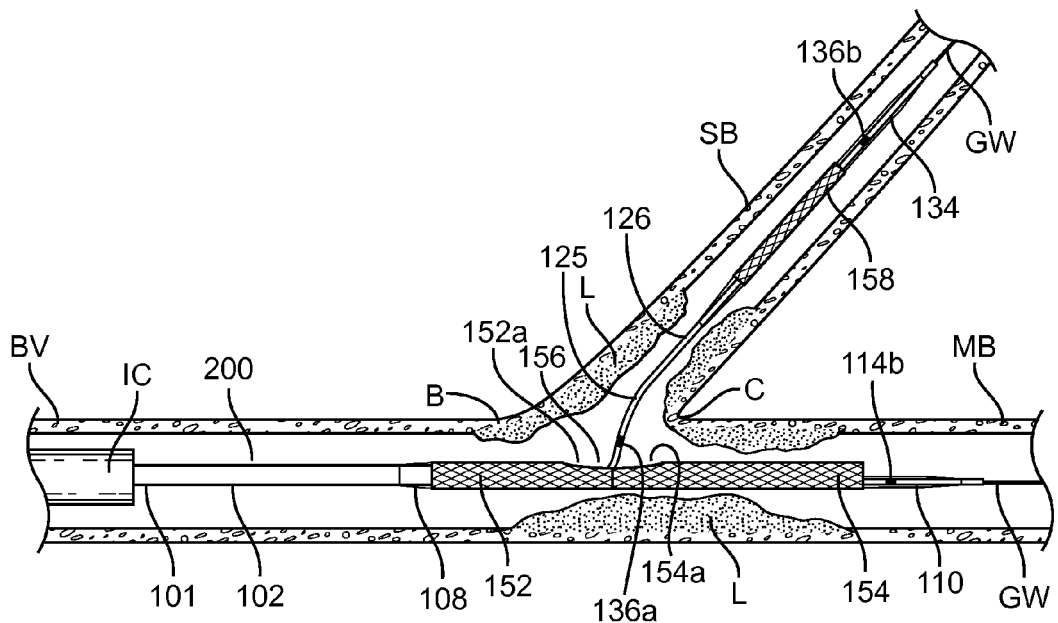

FIG. 6C shows the bifurcation treatment system 200 of FIG. 2 being advanced through the introducer catheter IC, over both guidewires GW. Both catheters 101, 125 are advanced distally until they engage the carina C, resisting further distal advancement. Both catheters may be advanced slightly distally, or retracted slightly proximally such that the first catheter 101 is positioned in the main branch MB with the proximal stent 152 at least partially upstream of the bifurcation B, and the distal stent 154 is at least partially downstream of the bifurcation B. Both stents 152, 154 of course will be aligned with the lesion L in the main branch MB. Furthermore, the notched regions 152a, 154a forming the side hole 156 will also be aligned with the ostium to the side branch. The second catheter 125 is positioned in the side branch SB, preferably such that stent 158 is slightly distal to the side branch lesion L. In this embodiment, the stents 152, 154, 158 are preferably balloon expandable. However, they may also be self-expanding, or combinations of balloon expandable and self-expanding.

Figure 6D:
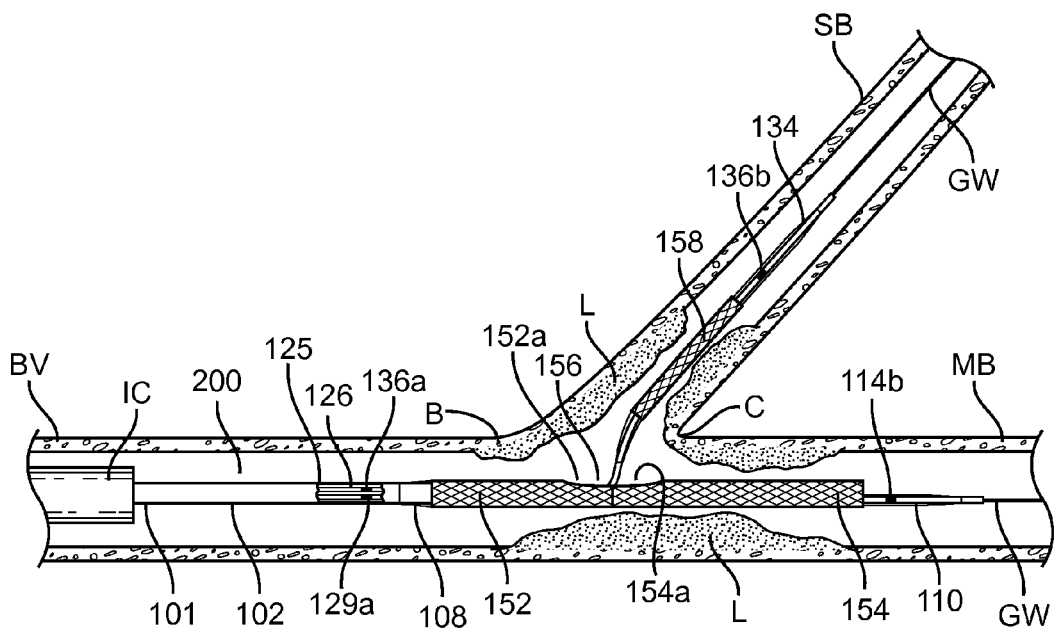

FIG. 6D illustrates an optional step wherein the second catheter 125 is proximally retracted through a lumen (not shown) in the first catheter 101 so that proximal radiopaque marker 136a on the second catheter 125 is aligned with proximal radiopaque marker 129a on the first catheter 101. This may be seen in the partial cutaway in FIG. 6D. Thus, a portion of shaft 126 slides under proximal balloon 108, under proximal stent 152, and through the shaft 102 of the first catheter 101. Furthermore, this ensures alignment of stent 158 with the side branch lesion L, with the ostium of the side branch, and with the proximal 152 and distal 154 balloons. This aspect of the procedure, as well as any other aspect of the procedure may be visualized using fluoroscopy, ultrasound, or other imaging techniques suitable for catheterization procedures.

Figure 6E:
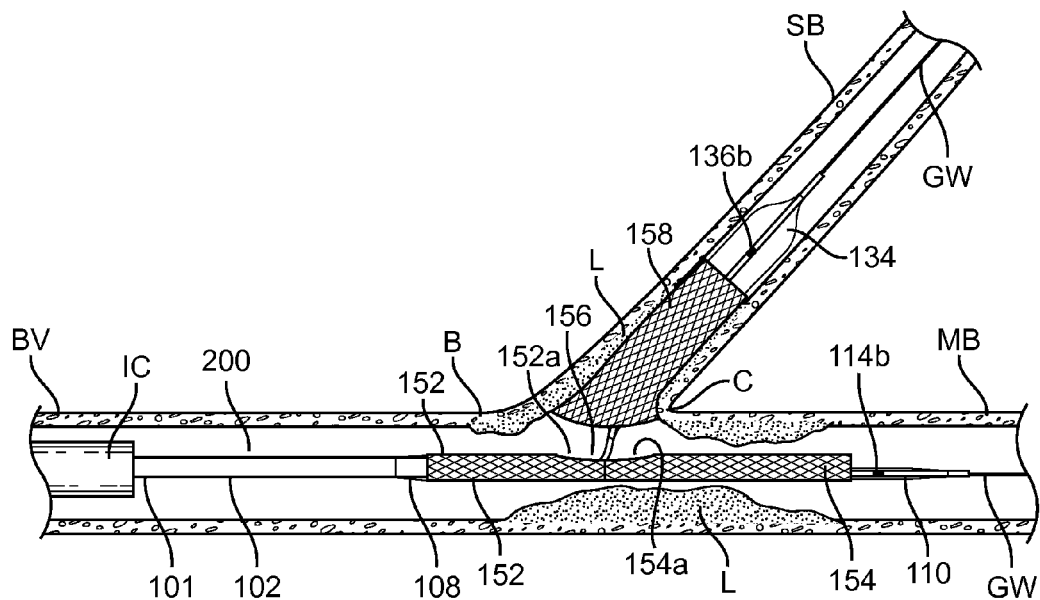

Once the stents on both catheters are properly aligned with the lesion, the bifurcation, and with one another, the balloons may be radially expanded thereby expanding the stents to treat the lesion. FIG. 6E illustrates a preferred first inflation wherein the balloon 134 on the second catheter 125 is expanded, thereby expanding stent 158 into the lesion L in the side branch SB. The balloon 134 may be inflated with saline, contrast media, combinations thereof, or with other fluids. The balloons are inflated to similar pressures as those previously described above. Of course, one of skill in the art will appreciate that these pressures are not limiting, and a physician may inflate the balloon to any desired pressure. After the stent is expanded into the lesion, the balloon 134 is deflated. A second post-dilation may also be performed if necessary to further tack the stent into position.

Figure 6F:
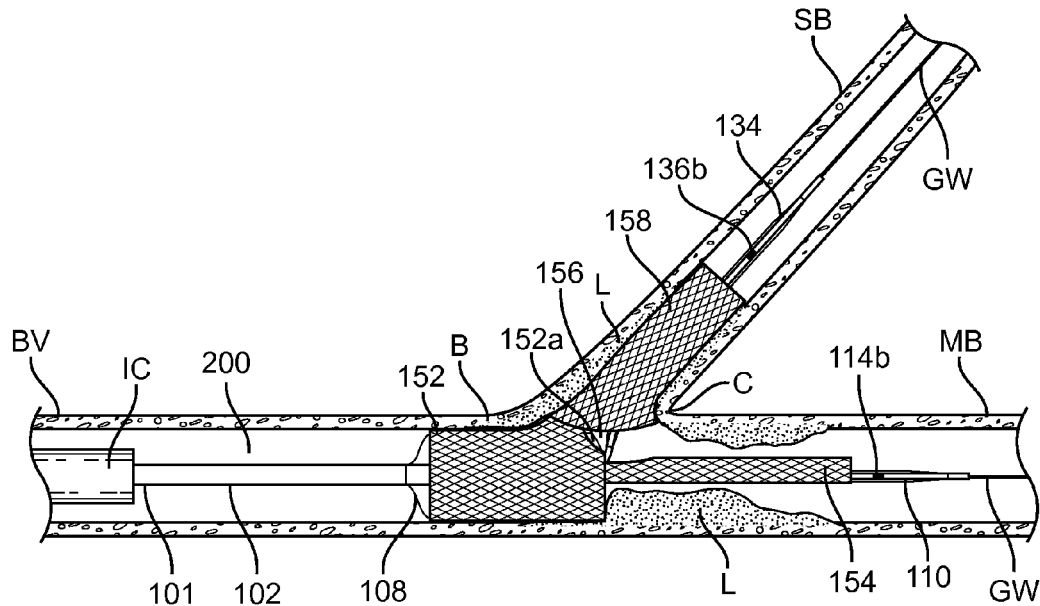
Figure 6G:
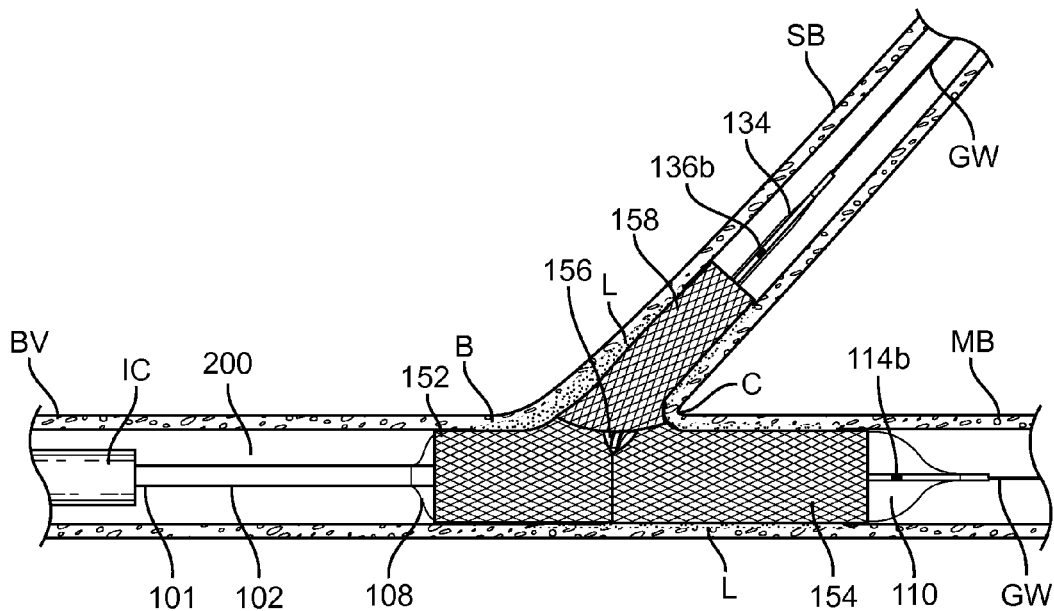

FIG. 6F illustrates another preferred step, wherein the proximal balloon 108 is expanded next so as to radially expand the proximal stent 152 into the lesion L around the lesion and slightly upstream of the bifurcation. Expansion of stent 152 is performed after expansion of stent 158 in the side branch SB. The proximal balloon may be inflated with similar fluids and pressures as previously described above. FIG. 6G illustrates the next preferred step wherein the distal balloon 110 is expanded using similar fluids and pressures as described above, thereby expanding distal stent 154. The distal balloon is inflated while the proximal balloon is inflated. Expansion of both proximal 108 and distal 110 balloons is a modified "kissing" balloon technique. Even though the balloons 108, 110 are separated by a gap, after inflation, the proximal end of the distal balloon 110 expands toward and abuts the distal end of the proximal balloon 108 which also advances toward the other balloon. Additional details on this are disclosed below in reference to FIGS. 8, and 9A-9B. This helps ensure that the distal end of the proximal stent 152 abuts the proximal end of the distal stent 154, and that the side hole 156 abuts the proximal end of the side branch stent 158, thereby ensuring that the stent fully covers and scaffolds the bifurcation. Additionally, expanding both the proximal and distal balloons 108, 110 ensures that the proximal and distal stents 152, 154 are expanded uniformly in the main branch, both upstream and downstream of the bifurcation. Optionally, the side branch balloon 134 may also be simultaneously expanded (not illustrated) so that all three balloons "kiss" with one another.

Figure 6H:
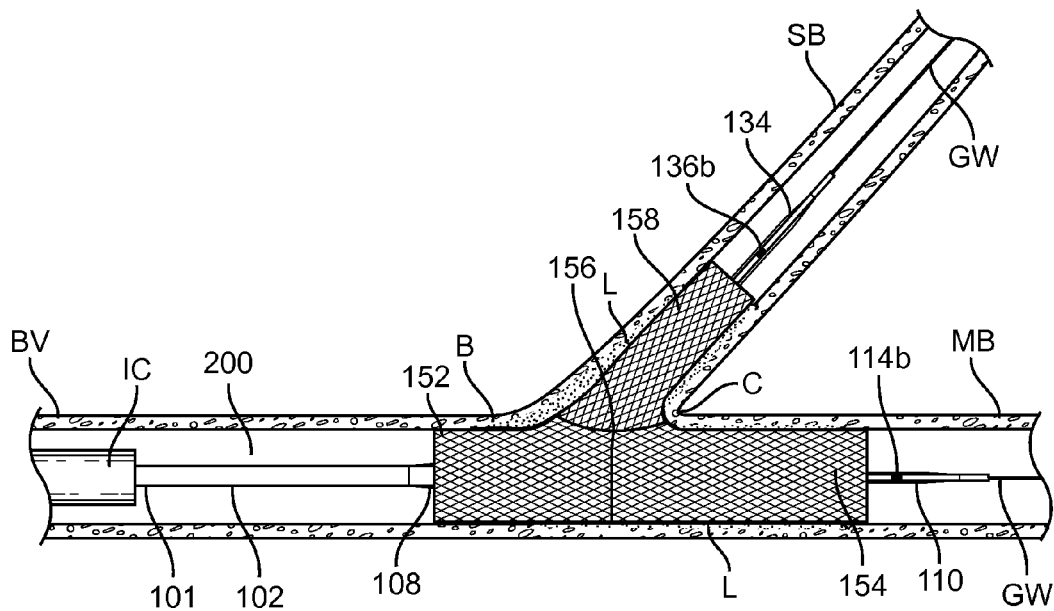
Figure 6I:
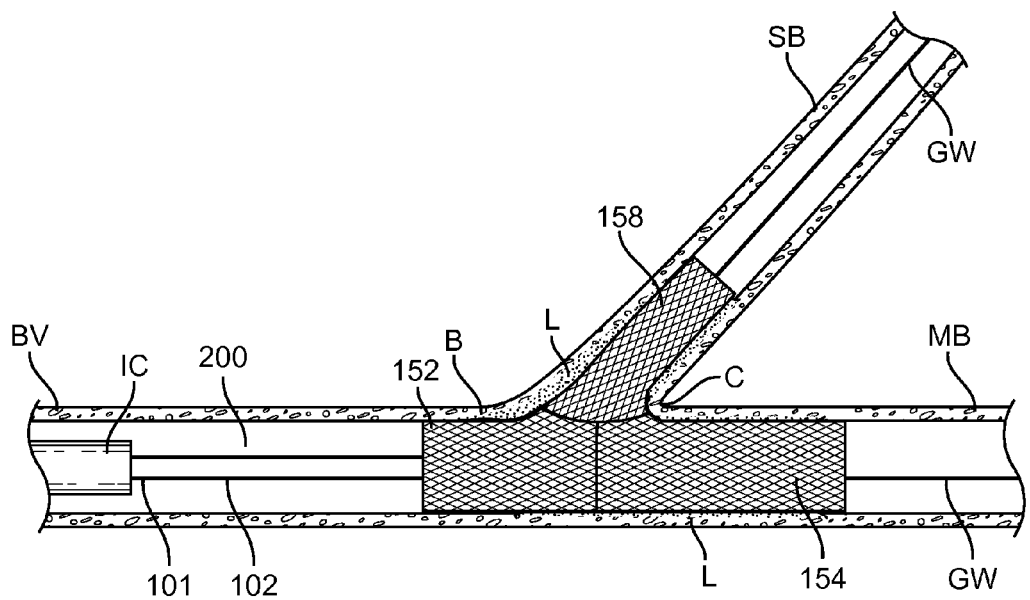
Figure 6J:
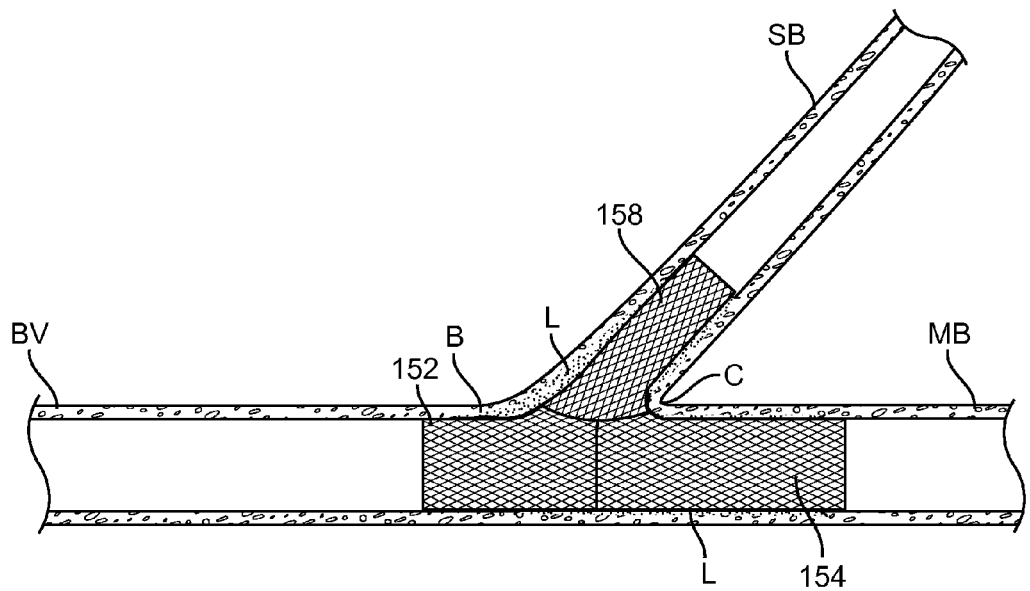

After the lesion has been successfully stented, both proximal and distal balloons 108, 110 (and side branch balloon 134, if also expanded) are deflated as illustrated in FIG. 6H. In FIG. 6I, both catheters 101, 125 are proximally retracted away from the bifurcation, and removed from the patient's body. Finally, in FIG. 6J, both guidewires GW and the introducer guidecatheter IC are also proximally retracted away from the bifurcation and removed from the patient's body. The blockage in the lumen is now substantially reduced and scaffolded, thereby improving blood flow across the bifurcation.

The exemplary method described above is not intended to be limiting. One of skill in the art will appreciate that a number of variations or changes may also be made. For example, any one or more of the balloons, stents, or combinations of balloons/stents may be coated with a therapeutic agent such as an anti-restonois drug like rapamycin, everolimus, biolimus A9, other analogs of rapamycin, or paclitaxel to help reduce restenosis. Moreover, any order or combination of balloon/stent expansion may be employed. For example, the proximal and distal balloons/stents may be expanded prior to expansion of the side branch balloon/stent, or the distal balloon/stent maybe inflated before the proximal balloon/stent. Other variations may include simultaneous expansion of the side branch balloon/stent with the proximal balloon/stent, or simultaneous inflation of the side branch balloon/stent and the distal balloon/stent. Any number of permutations are contemplated.

Figure 7:
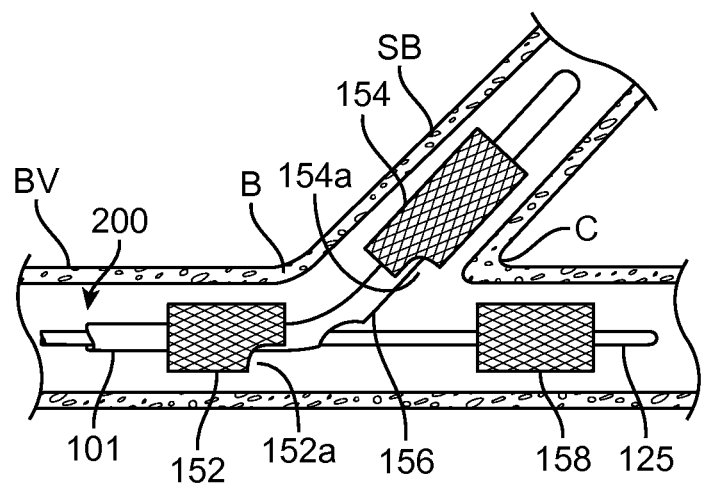
FIG. 7 illustrates another exemplary method of stenting a bifurcation.

Additionally, in an alternative embodiment shown in FIG. 7, the distal stent 154 of the first catheter 101 may be advanced into the side branch SB while the proximal stent 152 remains in the main branch MB. The stent 158 on the second catheter 125 may then be advanced into the main MB branch at least partially downstream of the bifurcation. Inflation of the balloons may follow any of the number of permutations discussed above.

Exemplary Balloon Configurations

Figure 8:
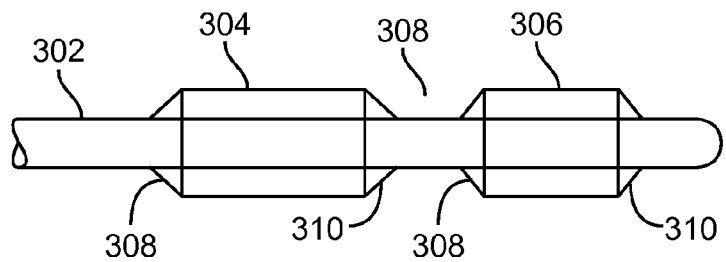
FIG. 8 illustrates an exemplary balloon configuration.

FIG. 8 illustrates one exemplary balloon configuration that may be used in any of the systems or method described above. Catheter shaft 302 includes a proximal balloon 304 and a distal balloon 306 coupled to the shaft 302. Both proximal and distal balloons 304, 306 have standard proximal tapers 308 and distal tapers 310. The tapered regions 308, 310 allow the balloon to be fixedly coupled to shaft 302 with a fluid tight seal. This may be accomplished by ultrasonic welding, adhesively bonding, suture wrapping, or other techniques known to those in the art. While this configuration is promising, the gap 308 separating the proximal and distal balloons 304, 306 will remain even after both balloons are inflated. Thus, a section of the vessel may remain undilated, or unstented, which is not optimal.

Figure 9A:
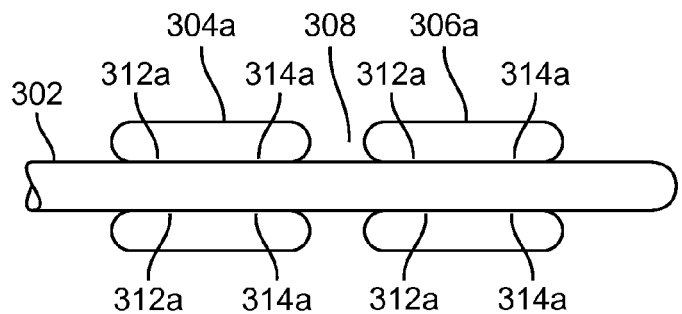
FIGS. 9A-9B illustrate an alternative embodiment of a balloon configuration.
Figure 9B:
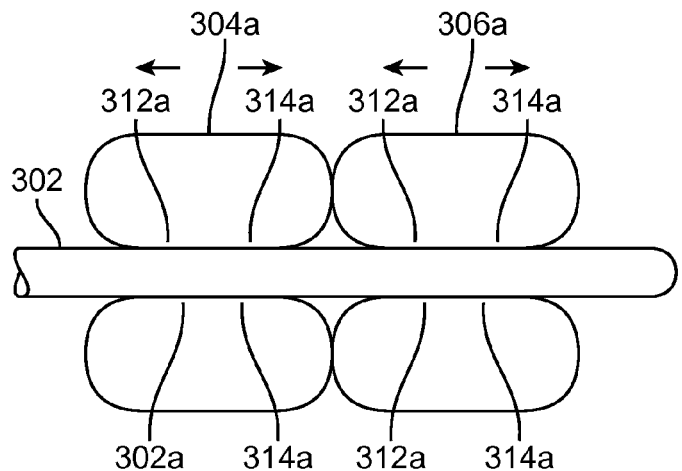

FIG. 9A illustrates another exemplary balloon configuration that may overcome some of the shortcomings of the previous embodiment. Shaft 302 includes a proximal balloon 304a and a distal balloon 306a. The proximal end 312a and the distal end 314a of each balloon is everted and attached to the shaft using similar techniques as those described above. In the unexpanded configuration of FIG. 9A, a gap 308 still exists when the balloons are uninflated. However, when both balloons 304a, 306a are inflated, because of the everted ends, the proximal end of each balloon will tend to move proximally, and the distal end of each balloon will also tend to move distally, as indicated by the arrows. Thus, the distal end of the proximal balloon 304a will move toward and abut the proximal end of the distal balloon 306a. This reduces or eliminates the gap 308 between the two balloons. Therefore, the vessel will be more uniformly dilated or stented. Also, in the case where stents are mounted over the balloons, the ends of the stents will also tend to move toward one another, therefore the gap between adjacent stents will also tend to close resulting in more uniform stenting.

Exemplary Stent Delivery Systems for Treating Trifurcations

Figure 10A:
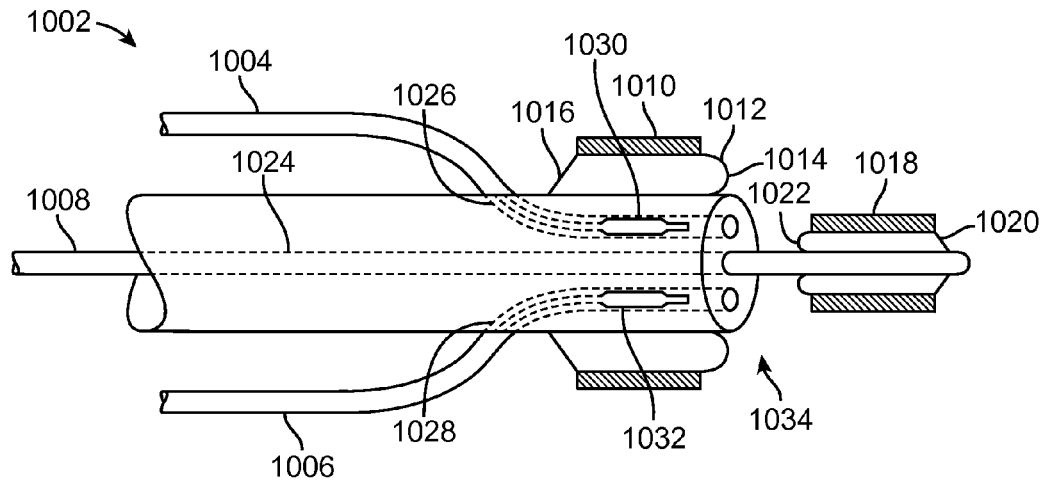
FIGS. 10A-10B illustrate an exemplary embodiment of stent delivery system for treating trifurcated vessels.
Figure 10B:
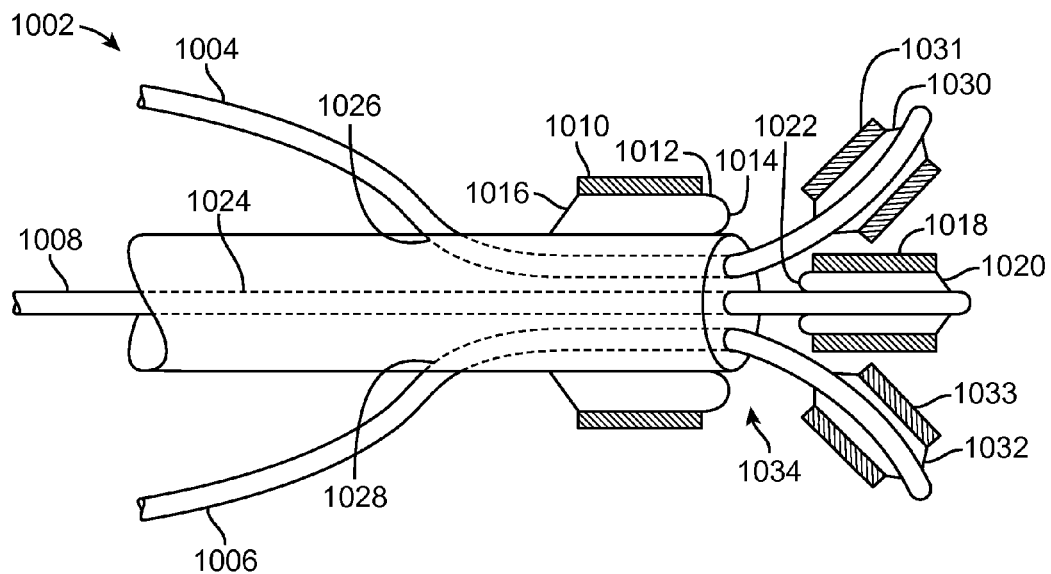

The embodiments described above are preferably used to treat bifurcated vessels. However, the basic embodiment may be expanded upon in order to treat trifurcated vessels such that those with a main branch and two side branches. FIGS. 10A-10B illustrate one exemplary embodiment of a stent delivery system that may be used to stent a trifurcated vessel. Stent delivery system 1002 includes a first side branch stent delivery catheter 1004 and a second side branch stent delivery catheter 1006. Also, the main branch stent delivery catheter includes a proximal balloon 1012 with a stent 1010 disposed thereover, and a distal balloon with a stent 1018 disposed thereover and coupled to a central shaft 1008. The central shaft includes at least three lumens sized to accommodate the shafts of the first and second side branch catheters, and the main branch shaft. The shafts may be slidable disposed in the lumens, or they may be fixed. The first side branch stent delivery catheter includes a balloon 1030 and stent 1031 disposed thereover near the catheter distal end. It is disposed in a rapid exchange lumen of the main shaft such that the proximal port 1026 is closer to the distal end of the catheter than the proximal end of the catheter. The second side branch catheter is similarly configured and includes a balloon 1032 and a stent 1033 disposed thereover adjacent the distal end of the catheter. The second side branch catheter is disposed in a rapid exchange lumen of the main shaft such that the proximal port is closer to the distal end of the catheter than the proximal end. The main branch catheter includes proximal balloon 1012 having a proximal taper 1016 and a distal everted end 1014 that allows the distal end of the balloon to expand distally toward the distal main branch balloon upon inflation. In alternative embodiments, both ends of balloon 1012 may be tapered, everted, or the proxima end may be everted and the distal end may be tapered. The distal main branch balloon preferably includes a distal taper 1020 and a proximal everted end 1022 that moves proximally toward the proximal main branch balloon upon inflation. A gap 1034 separates the proximal main branch stent from the distal main branch stent, thereby creating a space for the first and second side branch catheters to extend therepast. The gap may be created with the notches or other stent geometries previously described above, with the exception that two notches are required to form two gaps. During delivery, the two side branch catheters may be slidably disposed in the lumens of the main branch catheter. Upon reaching the target trifurcated vessel, the two side branch catheters may be distally extended from the lumens and exposed, passing through the gap 1034 between the proximal and distal main branch stents. The balloons may be independently inflatable thereby allowing inflation in any order to deploy stents upstream and downstream of the trifurcation, and in the two sidebranches. Kissing balloons may also be used. In an alternative embodiments, one or more of the balloons may not include a stent, and thus the a portion of the trifurcation may be dilated and a portion of the trifurcation may be stented.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for treating a bifurcated vessel in a patient, the bifurcated vessel having a main branch and a side branch, said method comprising:

providing a first delivery catheter comprising a proximal first expandable member, a distal second expandable member, a proximal first stent, and a distal second stent,
wherein the proximal first expandable member and distal second expandable member are disposed close to or at a distal end of the first delivery catheter,
wherein the proximal first stent and the distal second stent are discrete stents, the proximal first stent disposed over the proximal first expandable member, and the distal second stent disposed over the distal second expandable member, and
wherein a distal portion of the proximal first stent comprises a notched region, and a proximal portion of the distal second stent comprises a notched region, the notched regions being cut out portions of the distal portion of the proximal first stent and the proximal portion of the distal second stent, respectively, and the notched regions being adjacent one another to form a side hole in the proximal first stent and the distal second stent;

providing a second delivery catheter comprising a third expandable member and a third stent, the third expandable member disposed close to or at a distal end of the second delivery catheter,
wherein the third stent is disposed over the third expandable member, and
wherein the second delivery catheter passes through the side hole in the proximal first stent and the distal second stent;

advancing the first delivery catheter and the second delivery catheter toward the bifurcation;

positioning the proximal first stent, the distal second stent, and the third stent at the bifurcation such that the proximal first stent is disposed in the main branch, the distal second stent is disposed in the side branch, and the third stent is disposed in the main branch downstream of the bifurcation,
wherein the side hole in the proximal first stent and the distal second stent is aligned with the main branch and faces downstream of the bifurcation;

radially expanding the distal second stent from a collapsed configuration to an expanded configuration;

radially expanding the proximal first stent from a collapsed configuration to an expanded configuration; and radially expanding the third stent from a collapsed configuration to an expanded configuration.

2. The method of claim 1, wherein positioning the proximal first stent, the distal second stent, and the third stent comprises advancing the first delivery catheter and the second delivery catheter until one or more of the delivery catheters engage a carina of the bifurcation.

3. The method of claim 1, wherein radially expanding the distal second stent comprises expanding the distal second stent to engage a wall of the side branch.

4. The method of claim 1, wherein radially expanding the distal second stent comprises expanding the distal second expandable member.

5. The method of claim 4, wherein the distal second expandable member comprises a balloon, and expanding the distal second expandable member comprises inflating the balloon.

6. The method of claim 1, wherein radially expanding the proximal first stent comprises expanding the proximal first stent to engage a wall of the main branch.

7. The method of claim 1, wherein radially expanding the proximal first stent comprise expanding the proximal first expandable member.

8. The method of claim 7, wherein the proximal first expandable member comprises a balloon, and expanding the proximal first expandable member comprises inflating the balloon.

9. The method of claim 1, wherein the proximal first stent is radially expanded before radial expansion of the distal second stent.

10. The method of claim 1, wherein radially expanding the third stent comprises expanding the third stent to engage a wall of the main branch.

11. The method of claim 10, wherein radially expanding the third stent comprises expanding the third expandable member.

12. The method of claim 11, wherein the third expandable member comprises a balloon, and expanding the third expandable member comprises inflating the balloon.

13. The method of claim 1, wherein the third stent is radially expanded after radial expansion of the proximal first stent and the distal second stent.

14. The method of claim 1, further comprising proximally retracting the second delivery catheter so that a proximal end of the third stent is aligned with the side hole in the proximal first stent and the distal second stent.

15. The method of claim 14, wherein proximally retracting the second delivery catheter comprises aligning a radiopaque maker on the second delivery catheter with a radiopaque marker on the first delivery catheter.

16. The method of claim 14, wherein proximally retracting the second delivery catheter comprises sliding the second delivery catheter under a portion of the proximal first stent.

17. The method of claim 16, wherein proximally retracting the second delivery catheter comprises sliding the second delivery catheter through the side hole in the proximal first stent and the distal second stent.

18. The method of claim 1, wherein a proximal portion of the third stent abuts a portion of the proximal first stent and a portion of the distal second stent, after radial expansion of the proximal first stent, the distal second stent, and the third stent.

19. The method of claim 18, wherein the distal portion of the proximal first stent abuts the proximal portion of the distal second stent after radial expansion thereof.

* * * * *

UNITED STATES PATENT AND TRADEMARK OFFICE
CERTIFICATE OF CORRECTION

PATENT NO. : 9,254,210 B2
APPLICATION NO. : 13/796466
DATED : February 9, 2016
INVENTOR(S) : Henry Bourang It is certified that error appears in the above-identified patent and that said Letters Patent is hereby corrected as shown below:

On the Title Page

In item (71), in "Applicant", in Column 1, Line 1, delete "Systems," and insert --Systems-- therefor In item (73), in "Assignee", in Column 1, Line 1, delete "Systems," and insert --Systems-- therefor Signed and Sealed this
Twenty-first Day of April, 2020

Andrei Iancu
*Director of the United States Patent and Trademark Office*